US009165112B2

(12) United States Patent         (10) Patent No.:     US 9,165,112 B2
     Doyle et al.                 (45) Date of Patent:     Oct. 20, 2015

(54) SYSTEMS AND METHODS FOR DISPLAYING OBJECTS AT A MEDICAL TREATMENT APPARATUS DISPLAY SCREEN

(75) Inventors: Matthew J. Doyle, Walnut Creek, CA (US); Nathan Parnell, San Francisco, CA (US); Alex Brown, Danville, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 97 days.

(21) Appl. No.: 13/365,714

(22) Filed: Feb. 3, 2012

(65) Prior Publication Data

US 2013/0201222 A1    Aug. 8, 2013

(51) Int. Cl.
    G06F 3/0486    (2013.01)
    G06F 19/00     (2011.01)
(52) U.S. Cl.
    CPC ................... *G06F 19/3406* (2013.01)
(58) Field of Classification Search
    CPC ............ G09G 5/32; G06F 3/048; G06F 3/01; G06F 3/00; G06F 17/24; A61B 5/00; A61B 5/055; A61B 1/00
    USPC .................. 345/440, 661, 672; 600/300, 407; 715/741, 744, 765, 771; 705/2
    See application file for complete search history.

(56) References Cited

U.S. PATENT DOCUMENTS

| 3,871,913 A | 3/1975 | Shaldon |
| 4,174,231 A | 11/1979 | Hobgood |
| 4,191,351 A | 3/1980 | Goyne |
| 4,581,141 A | 4/1986 | Ash |
| 4,661,246 A | 4/1987 | Ash |
| 4,666,598 A | 5/1987 | Heath et al. |
| 4,684,460 A | 8/1987 | Issautier |

(Continued)

FOREIGN PATENT DOCUMENTS

| EP | 0278100 | 8/1988 |
| EP | 0673658 | 9/1995 |

(Continued)

OTHER PUBLICATIONS

"RX Guide to Custom Dialysis," COBE Renal Care Inc., Revision E. Sep. 1993.

(Continued)

*Primary Examiner* — Ulka Chauhan
*Assistant Examiner* — Michael Le
(74) *Attorney, Agent, or Firm* — Onello & Mello, LLP

(57) ABSTRACT

System and methods are provided for displaying objects at a treatment display screen coupled to an apparatus for performing a treatment. A first arrangement of the objects is presented at the treatment display screen. At least some objects of the first arrangement of the objects are in a fixed state on the treatment display screen. A rearrangement mode of operation of the treatment display screen is activated. The objects of the first arrangement of the objects are changed from the fixed state to a fluid state that allows for rearrangement of the objects of the first arrangement of the objects to a second arrangement of the objects that is different than the first arrangement of the objects. The treatment is prevented from being performed during operation in the rearrangement mode. The second arrangement of the objects is presented at the treatment display screen during operation in the rearrangement mode.

39 Claims, 12 Drawing Sheets

(56) References Cited

U.S. PATENT DOCUMENTS

| | | | |
|---|---|---|---|
| 4,728,496 A | 3/1988 | Petersen et al. | |
| 4,770,787 A | 9/1988 | Heath et al. | |
| 4,784,495 A | 11/1988 | Jonsson et al. | |
| 4,789,467 A | 12/1988 | Lindsay et al. | |
| 4,997,577 A | 3/1991 | Stewart | |
| 5,256,371 A | 10/1993 | Pippert | |
| 5,262,068 A | 11/1993 | Bowers et al. | |
| 5,277,820 A | 1/1994 | Ash | |
| 5,304,349 A | 4/1994 | Polaschegg | |
| 5,409,612 A | 4/1995 | Maltais et al. | |
| 5,421,813 A | 6/1995 | Ohnishi | |
| 5,473,536 A | 12/1995 | Wimmer | |
| 5,536,412 A | 7/1996 | Ash | |
| 5,589,070 A | 12/1996 | Maltais et al. | |
| 5,591,344 A | 1/1997 | Kenley et al. | |
| 5,603,902 A | 2/1997 | Maltais et al. | |
| 5,605,630 A | 2/1997 | Shibata | |
| 5,620,608 A | 4/1997 | Rosa et al. | |
| 5,643,212 A | 7/1997 | Coutre et al. | |
| 5,713,125 A | 2/1998 | Watanabe et al. | |
| 5,788,099 A | 8/1998 | Treu et al. | |
| 5,835,916 A * | 11/1998 | Inaki et al. | 715/212 |
| 5,919,369 A | 7/1999 | Ash | |
| 5,944,684 A | 8/1999 | Roberts et al. | |
| 6,000,567 A | 12/1999 | Carlsson et al. | |
| 6,036,858 A | 3/2000 | Carlsson et al. | |
| 6,086,753 A | 7/2000 | Ericson et al. | |
| 6,143,181 A | 11/2000 | Falkvall et al. | |
| 6,170,785 B1 | 1/2001 | Lampropoulos et al. | |
| 6,188,407 B1 | 2/2001 | Smith et al. | |
| 6,190,855 B1 | 2/2001 | Herman et al. | |
| 6,277,277 B1 | 8/2001 | Jacobi et al. | |
| 6,280,632 B1 | 8/2001 | Polaschegg | |
| 6,308,721 B1 | 10/2001 | Bock et al. | |
| 6,409,699 B1 | 6/2002 | Ash | |
| 6,411,836 B1 | 6/2002 | Patel et al. | |
| 6,416,293 B1 | 7/2002 | Bouchard et al. | |
| 6,428,706 B1 | 8/2002 | Rosenqvist et al. | |
| 6,627,164 B1 | 9/2003 | Wong | |
| 6,755,976 B2 | 6/2004 | Rosenqvist et al. | |
| 6,775,577 B2 * | 8/2004 | Crnkovich et al. | 700/11 |
| 6,818,196 B2 | 11/2004 | Wong | |
| 6,878,283 B2 | 4/2005 | Thompson | |
| 7,033,498 B2 | 4/2006 | Wong | |
| 7,077,956 B2 | 7/2006 | Rovatti | |
| 7,101,519 B2 | 9/2006 | Wong | |
| 7,169,303 B2 | 1/2007 | Sullivan et al. | |
| 7,241,272 B2 | 7/2007 | Karoor et al. | |
| 7,273,465 B2 | 9/2007 | Ash | |
| 7,566,432 B2 | 7/2009 | Wong | |
| 7,867,214 B2 | 1/2011 | Childers et al. | |
| 7,899,683 B2 | 3/2011 | Schoenberg et al. | |
| 7,904,824 B2 | 3/2011 | Stern et al. | |
| 8,029,454 B2 | 10/2011 | Kelly et al. | |
| 2002/0001794 A1 | 1/2002 | Melker et al. | |
| 2002/0079695 A1 | 6/2002 | Campbell et al. | |
| 2002/0138512 A1 | 9/2002 | Buresh et al. | |
| 2004/0019312 A1 | 1/2004 | Childers et al. | |
| 2004/0022717 A1 | 2/2004 | Wong | |
| 2004/0050789 A1 | 3/2004 | Ash | |
| 2004/0070201 A1 | 4/2004 | Niermeyer et al. | |
| 2005/0031523 A1 | 2/2005 | Wong | |
| 2005/0131332 A1 | 6/2005 | Kelly et al. | |
| 2005/0274658 A1 | 12/2005 | Rosenbaum et al. | |
| 2006/0287831 A1 * | 12/2006 | Totiba et al. | 702/19 |
| 2007/0158247 A1 | 7/2007 | Carr et al. | |
| 2007/0158249 A1 | 7/2007 | Ash | |
| 2007/0158268 A1 | 7/2007 | DeComo | |
| 2007/0161113 A1 | 7/2007 | Ash | |
| 2007/0161941 A1 | 7/2007 | Ash et al. | |
| 2007/0179431 A1 | 8/2007 | Roberts et al. | |
| 2007/0181499 A1 | 8/2007 | Roberts et al. | |
| 2008/0149563 A1 | 6/2008 | Ash | |
| 2008/0177216 A1 | 7/2008 | Ash | |
| 2009/0037216 A1 | 2/2009 | Bluemler et al. | |
| 2009/0061404 A1 | 3/2009 | Toly | |
| 2009/0127193 A1 | 5/2009 | Updyke et al. | |
| 2009/0222119 A1 | 9/2009 | Plahey et al. | |
| 2010/0131883 A1 * | 5/2010 | Linthicum et al. | 715/771 |
| 2011/0000832 A1 | 1/2011 | Kelly et al. | |
| 2011/0004351 A1 | 1/2011 | Kelly et al. | |
| 2011/0005986 A1 | 1/2011 | Kelly et al. | |
| 2011/0005992 A1 | 1/2011 | Kelly et al. | |
| 2011/0009797 A1 | 1/2011 | Kelly et al. | |
| 2011/0009798 A1 | 1/2011 | Kelly et al. | |
| 2011/0017665 A1 | 1/2011 | Updyke et al. | |
| 2011/0077470 A1 | 3/2011 | Hussain et al. | |
| 2011/0105983 A1 | 5/2011 | Kelly et al. | |
| 2011/0160637 A1 | 6/2011 | Beiriger | |
| 2011/0204092 A1 | 8/2011 | Niermeyer et al. | |
| 2011/0297593 A1 | 12/2011 | Kelly et al. | |
| 2011/0303588 A1 | 12/2011 | Kelly et al. | |
| 2012/0018378 A1 | 1/2012 | Kelly et al. | |
| 2012/0022441 A1 | 1/2012 | Kelly et al. | |
| 2012/0043279 A1 | 2/2012 | Kelly et al. | |
| 2012/0085707 A1 | 4/2012 | Beiriger | |
| 2012/0138533 A1 | 6/2012 | Curtis et al. | |

FOREIGN PATENT DOCUMENTS

| | | |
|---|---|---|
| EP | 1096991 | 5/2001 |
| EP | 1170659 A2 | 1/2002 |
| EP | 1342480 | 9/2003 |
| EP | 1426912 | 6/2004 |
| EP | 2087916 | 8/2009 |
| GB | 2124511 | 2/1984 |
| WO | 9702055 | 1/1997 |
| WO | 9702056 | 1/1997 |
| WO | 9817333 | 4/1998 |
| WO | 9841267 A1 | 9/1998 |
| WO | 9937342 | 7/1999 |
| WO | 0002650 | 1/2000 |
| WO | 0230267 | 4/2002 |
| WO | 0243859 | 6/2002 |
| WO | 2004009158 | 1/2004 |
| WO | 2004105589 | 12/2004 |
| WO | 2005044339 | 5/2005 |
| WO | 2005123230 | 12/2005 |
| WO | 2007028056 | 3/2007 |
| WO | 2007081383 | 7/2007 |
| WO | 2007081384 | 7/2007 |
| WO | 2007081565 | 7/2007 |
| WO | 2007081576 | 7/2007 |

OTHER PUBLICATIONS

"Sorbent Dialysis Primer," COBE Renal Care, Inc., Sep. 4, 1993 Ed. 4.

Blumenkrantz, et al., "Applications of the Redy Sorbent System to Hemodialysis and Peritoneal Dialysis;" Artificial Organs, 3(3):230-236, 1978.

Operator's Manual—Fresenius 2008K Hemodialysis Machine (2000).

Hans-Dietrich Polaschegg, "Neglected Safety Aspects in Hemodialysis Machines and Their Related Problems;" Hemodialysis Horizons, pp. 65-68.

Madhukar Misra, "The basics of hemodialysis equipment;" Hemodialysis International 2005; 9: pp. 30-36.

"Systems and Method for Providing Notifications in Dialysis Systems" Specification, Drawings, Claims and Prosecution History, of U.S. Appl. No. 13/299,790, filed Nov. 18, 2011, by Matthew J. Doyle.

"Systems and Methods for Compensation of Compliant Behavior in Regenerative Dialysis Systems" Specification, Drawings, Claims and Prosecution History, of U.S. Appl. No. 12/902,702, filed Oct. 12, 2010, by Matthew J. Doyle.

International Search Report and Written Opinion issued on May 14, 2013 in related International Application No. PCT/US2012/065248.

International Search Report and Written Opinion issued on Jul. 9, 2013 in related International Application No. PCT/US2013/024361.

PCT International Search Report and Written Opinion dated Apr. 15, 2014 issued in corresponding PCT Application No. US 2013/076967.

* cited by examiner

SYSTEMS AND METHODS FOR DISPLAYING OBJECTS AT A MEDICAL TREATMENT APPARATUS DISPLAY SCREEN

BACKGROUND

Hemodialysis machines are well-known for treating medical conditions related to renal failure, where a person's kidneys inadequately filter toxins and waste products from the blood. During a hemodialysis procedure, blood is removed from the patient and output to a dialyzer associated with the hemodialysis machine. The patient's blood circulates along one side of a semipermeable membrane in the dialyzer, referred to as an extracorporeal circuit (ECC). A dialysate is provided by a dialysate system, and flows between the dialysate system and the hemodialysis machine along the opposite side of the membrane, referred to as a dialysate circuit, to remove waste, toxins, and other undesirable products from the blood. In a regenerative dialysis system, the used dialysate is pumped through a sorbent cartridge at the dialysate system, which purifies the dialysate by removing the waste so that a constant stream of fresh dialysate is provided to the dialyzer. In a non-regenerative dialysis system, the used dialysate is discarded.

A hemodialysis machine typically includes various meters, sensors, and other event detection and monitoring systems positioned along the ECC and the dialysate circuit to monitor an array of safety-critical parameters and to detect abnormal events occurring prior to or during a dialysis procedure. Safety-critical parameters can include, but are not limited to, blood and dialysate flow rates, temperature, venous and arterial pressure, and dialysis solution conductivity. Parameter-related information is received at a control panel in communication with the hemodialysis machine, and presented as text, graphics, and the like at a control panel monitor, touch-screen, or other display. A set of screens, windows, and the like, can be presented at the display, which are populated with parameters or related information in the form of static or discrete objects, for example, graphical user interface (GUI) objects displayed as data buttons, keys, windows, icons, bar graphs, charts, and the like. One type of screen is a treatment display screen, which permits an operator to set and monitor treatment parameters before or during a dialysis procedure. Parameter buttons and other static objects are arranged at fixed locations of each treatment display screen. Static treatment display screen configurations are provided to maintain dialysis machine efficacy during operation and to provide a safe environment for a patient undergoing a dialysis procedure.

BRIEF SUMMARY

In accordance with one aspect, a computer-implemented method is provided for displaying objects at a treatment display screen coupled to an apparatus for performing a treatment. The method comprises presenting a first arrangement of the objects at the treatment display screen, wherein the objects of the first arrangement of the objects are in a fixed state on the treatment display screen; activating a rearrangement mode of operation of the treatment display screen, wherein the objects of the first arrangement of the objects are changed from the fixed state to a fluid state that allows for rearrangement of the objects of the first arrangement of the objects to a second arrangement of the objects that is different than the first arrangement of the objects; preventing the treatment from being performed during operation in the rearrangement mode; and presenting the second arrangement of the objects at the treatment display screen during operation in the rearrangement mode.

In an embodiment, the treatment includes a dialysis-related procedure.

In an embodiment, activating the rearrangement mode of operation comprises generating a unique key sequence.

In an embodiment, preventing the treatment from being performed comprises preventing an initiation of a treatment clock button displayed at the treatment display screen.

In an embodiment, the apparatus includes a dialysis system, and the method further comprises detecting a treatment-related event and preventing the first arrangement of the objects from transitioning from the fixed state to the fluid state in response to detecting the treatment-related event.

In an embodiment, detecting the treatment-related event includes detecting blood in the dialysis system.

In an embodiment, detecting the treatment-related event includes detecting activation of a treatment clock button displayed at the treatment display screen.

In an embodiment, the method further comprises, during operation in the rearrangement mode: determining a period of inactivity during which the objects remain at their current locations at the treatment display screen; and placing the objects in the fixed state in response to the period of inactivity.

In an embodiment, the method further comprises storing data related to the second arrangement of the objects; displaying a set of configuration options, a configuration option including the stored data related to the second arrangement of the objects; and selecting a configuration option from the configuration options.

In an embodiment, the configuration options are displayed in response to at least one of a power-related condition of a machine performing the treatment, an initialization of the treatment, and an activation of a treatment clock button displayed at the treatment display screen.

In an embodiment, the set of configuration options includes a default configuration.

In an embodiment, the method further comprises identifying the configuration option including the stored data related to the second arrangement of the objects as being a recently used configuration.

In an embodiment, presenting the second arrangement of the objects at the treatment display screen comprises determining that a first object in the fluid state is positioned on a second object, generating an object repository identified by a subscreen button, and placing the first object and the second object in the object repository.

In an embodiment, presenting the second arrangement of the objects at the treatment display screen comprises moving a first object of the first arrangement of objects from a first location at the treatment display screen to a second location at the treatment display screen and repositioning a second object at the second location to another location.

In an embodiment, repositioning the second object at the second location to another location comprises repositioning the second object at the second location to a location neighboring the second location.

In an embodiment, the first object and the second object are interchanged.

In an embodiment, the computer-implemented method further comprises assigning the objects to a display matrix at the treatment display screen, the display matrix comprising a plurality of columns and a plurality of rows; and determining a column and a row of the display matrix at which the first location and the second location are positioned, wherein moving the first object includes forming a vacancy at the first location, and wherein the vacancy at the first location is removed by moving an object adjacent the first location to the first location.

In an embodiment, the first object is moved to the column of the second location that is positioned to the left of the column of the first location, and wherein the second object is moved in a right direction of the treatment display screen.

In an embodiment, the first object is moved to the column of the second location that is positioned to the right of the column of the first location, and wherein the second object is moved in a left direction of the treatment display screen.

In an embodiment, the first object is moved to the row of the second location that is positioned above the column of the first location, and wherein the second object is moved in a down direction of the treatment display screen.

In an embodiment, the first object is moved to the row of the second location that is positioned below the column of the first location, and wherein the second object is moved in an up direction of the treatment display screen.

In an embodiment, after presenting the second arrangement of the objects at the treatment display screen: transitioning the second arrangement of the objects from the fluid state to a fixed state; and permitting performance of the treatment.

In accordance with another aspect, a computer-implemented method is provided for rearranging objects displayed at a treatment display screen. The method comprises displaying the objects having a fixed state; suspending a medical treatment; placing the objects into a fluid state; rearranging the objects at the treatment display screen; and transitioning the rearranged objects from the fluid state to the fixed state after rearranging the objects.

In an embodiment, the medical treatment includes a dialysis-related procedure.

In an embodiment, suspending the medical treatment comprises preventing an initiation of a treatment clock button displayed at the treatment display screen.

In an embodiment, placing the objects into the fluid state comprises generating a unique key sequence.

In an embodiment, the treatment display screen is in electronic communication with a dialysis system, and wherein the method further comprises detecting a treatment-related event and preventing the objects from entering the fluid state in response to detecting the treatment-related event.

In an embodiment, detecting the treatment-related event includes detecting blood in the dialysis system.

In an embodiment, detecting the treatment-related event includes detecting activation of a treatment clock button displayed at the treatment display screen.

In an embodiment, the method further comprises determining a period of inactivity during which the objects remain at their current locations at the treatment display screen, and placing the objects in the fixed state in response to the period of activity.

In an embodiment, the method further comprises storing data related to the objects, displaying a set of configuration options, a configuration option including the stored data related to the objects, and selecting a configuration option from the configuration options.

In an embodiment, the configuration options are displayed in response to at least one of a power-related condition of a machine performing the medical treatment, an initialization of the medical treatment, and an activation of a treatment clock button displayed at the treatment display screen.

In an embodiment, the set of configuration options includes a default configuration.

In an embodiment, the method further comprises identifying the configuration option including the stored data related to the rearranged objects as being a recently used configuration.

In an embodiment, rearranging the objects at the treatment display screen comprises determining that a first object in the fluid state is positioned on a second object, generating an object repository identified by a subscreen button, and placing the first object and the second object in the object repository.

In an embodiment, rearranging the objects at the treatment display screen comprises: moving a first object from a first location at the treatment display screen to a second location at the treatment display screen and repositioning a second object at the second location to another location.

In an embodiment, repositioning the second object at the second location to another location comprises repositioning the second object at the second location to a location neighboring the second location.

In an embodiment, the first object and the second object are interchanged.

In accordance with another aspect, a treatment display screen comprises a set of rearrangable objects, and a treatment clock button. The objects have a fixed state during a medical treatment. The objects have a fluid state during a rearrangement of the objects at the treatment display screen. The treatment clock button controls an activation of the medical treatment. The treatment clock button inactivated during presentation of the objects in the fluid state.

In an embodiment, after presentation of the objects in the fluid state, the treatment clock button is activated, the objects transition from the fluid state to the fixed state, and the medical treatment is permitted to be performed.

In an embodiment, the objects include graphical user interface (GUI) objects, including data buttons, keys, windows, icons, bar graphs, charts, or a combination thereof.

In an embodiment, the treatment display screen further comprises an electronic keyboard for entering a unique key sequence to inactivate the treatment clock button.

In an embodiment, the treatment display screen further comprises a subscreen button and an object repository identified by the subscreen button, wherein the subscreen button is displayed at the treatment display screen in response to a first object positioned on a second object during the rearrangement, and wherein the first object and the second object are positioned in the object repository.

In accordance with another aspect, a computer-implemented method is provided for rearranging a plurality of objects displayed at a treatment display screen. The method comprises transitioning a plurality of objects from a fixed state to a fluid state; moving a first object of the plurality of objects from a first location at the treatment display screen to a second location at the treatment display screen; positioning the first object on or near a second object at the second location of the treatment display screen; replacing the first object and the second object at the treatment display screen with a subscreen button at the second location of the treatment display screen; and redisplaying at least one of the first object and the second object at the second location of the treatment display screen in response to selecting the subscreen button.

In accordance with another aspect, a display object configuration system is provided for rearranging a plurality of objects displayed at a treatment display screen. The display object configuration system comprises an object state determination module, an object state modification module, and a key sequence processor. The object state determination module determines a state of the plurality of objects having a configuration arrangement at the treatment display screen. The state is one of a fixed state and a fluid state. The object state modification module activates a rearrangement mode of operation of the treatment display screen, and changes the state of the plurality of objects from the fixed state to the fluid state that allows for rearrangement of the objects. The key sequence processor inactivates a treatment clock for preventing a treatment from being performed during the rearrangement mode of operation.

In an embodiment, the display object configuration system further comprises a configuration repository that stores the configuration arrangement.

In an embodiment, the configuration repository stores other configuration arrangements of the plurality of objects.

In an embodiment, the display object configuration system further comprises a timeout inactivity module that determines a period of inactivity during which the objects remain at their current locations at the treatment display screen and places the objects in the fixed state in response to the period of inactivity.

In an embodiment, the display object configuration system further comprises a subscreen object generator that provides a subscreen button and an object repository identified by the subscreen button, wherein the subscreen button is displayed at the treatment display screen in response to a first object positioned on a second object during the rearrangement mode of operation, and the first object and the second object are positioned in the object repository.

In another aspect, a computer program product is provided for displaying objects at a treatment display screen coupled to an apparatus for performing a treatment. The computer program product comprises a computer readable storage medium having computer readable program code embodied therewith. The computer readable program code comprises computer readable program code configured to present a first arrangement of the objects at the treatment display screen, wherein the objects of the first arrangement of the objects are in a fixed state on the treatment display screen; computer readable program code configured to activate a rearrangement mode of operation of the treatment display screen, wherein the objects of the first arrangement of the objects are changed from the fixed state to a fluid state that allows for rearrangement of the objects of the first arrangement of the objects to a second arrangement of the objects that is different than the first arrangement of the objects; computer readable program code configured to prevent the treatment from being performed during operation in the rearrangement mode; and computer readable program code configured to present the second arrangement of the objects at the treatment display screen during operation in the rearrangement mode.

BRIEF DESCRIPTION

The above and further advantages of embodiments of the present inventive concepts may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
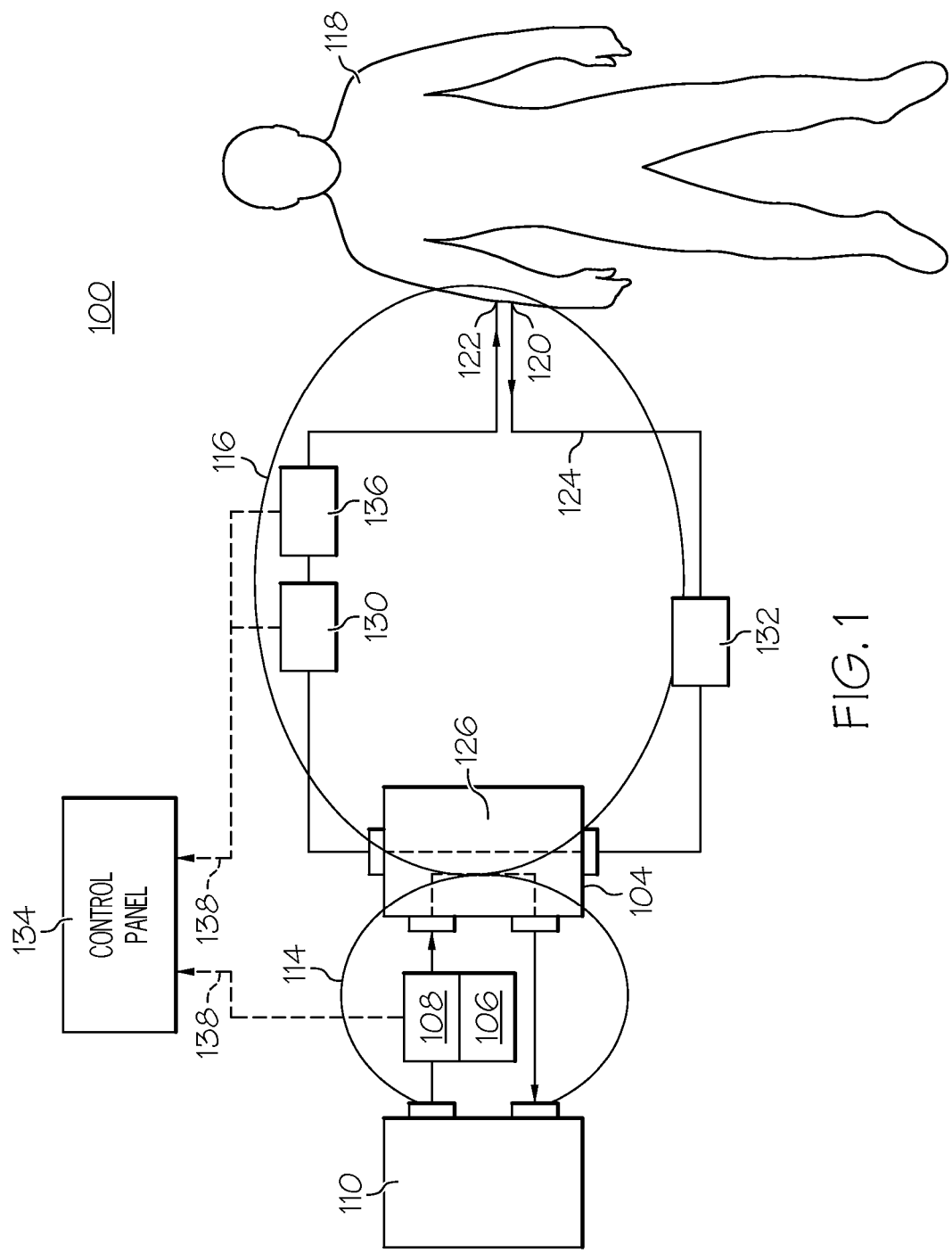
FIG. 1 is a schematic block diagram of a dialysis system, in which embodiments of the present inventive concepts can be practiced.

Embodiments will now be described more fully hereinafter with reference to the accompanying drawings, in which embodiments of the inventive concepts are shown. This invention may, however, be embodied in many different forms and should not be construed as limited to the embodiments set forth herein. Like numbers refer to like elements throughout.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. As used herein, the term "and/or" includes any and all combinations of one or more of the associated listed items and may be abbreviated as "/".

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent," etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

In brief overview, aspects of the present inventive concepts include systems and methods that provide an operator of a medical treatment apparatus such as a dialysis machine with the ability to rearrange parameter buttons, windows, graphs, charts, or other objects displayed on a treatment display screen in communication with the treatment apparatus. This is achieved at least in part by changing a state of the treatment display objects from a fixed state to a fluid, i.e., movable, state. In some embodiments, the state can be changed from fixed to fluid for a predetermined period of time. In some embodiments, the state can be changed in response to a command generated from an interface controlled by an operator. In some embodiments, during operation in the fluid state, the treatment display screen is prevented from controlling the apparatus to perform a medical treatment, for example, a kidney dialysis treatment or related renal care treatment. For example, during operation in the fluid state, a treatment operator can control which treatment display objects are presented at the display and control their relative positions on the display. This feature permits treatment device control panels to be customized on a per-operator basis. This feature can be useful to a medical technician, nurse, doctor, patient, or other user having personal preferences with respect to the manner in which treatment display objects are displayed when performing a treatment from the treatment display screen. This feature can also be useful in applications that include personal treatment systems, where customized display screen configurations are preferred. For example, the systems and methods can be applied to peritoneal, portable, home, wearable, or regenerative dialysis devices, such as the 2008K@home™ hemodialysis delivery system manufactured by Fresenius Medical Care AG & Co. In such applications, a treatment display screen can be preconfigured according to the patient's requirements, and reconfigured on an operator-by-operator basis. For example, different hospice workers may conduct a treatment, whereby each hospice worker can view a treatment display screen having objects arranged according to his or her personal preference, or according to a preference based on the specific requirements for a specific type of treatment.

The present inventive concepts provide additional safeguards to ensure patient safety with respect to rearranging buttons or other objects at a treatment display screen. In one embodiment, object rearrangement is prevented when certain events occur or during a particular timespan. For example, object rearrangement can be prevented when the treatment clock is running, when blood is sensed, or when other indicators of a treatment in progress are detected. Object rearrangement can also be prevented when certain machine-related conditions occur, such as a power failure or when the treatment clock displayed at the treatment display screen is re-initialized.

In another embodiment, a unique or special key sequence is required to change treatment display objects from a fixed state to a fluid state for rearrangement. The key sequence, when entered, can prevent an initiation of the treatment clock. Since a treatment is typically performed directly in response to the active state of the treatment clock, a user can be prevented from inadvertently attempting to perform a treatment while the objects are in a fluid state. The treatment display objects can automatically return to a fixed state at the end of a predetermined period of time suitable for such rearrangement, or when an inactivity timeout is detected during the predetermined period of time. Alternatively, the treatment display objects can return to the fixed state in response to an action by the operator, such as an entry of a key-sequence or code on the display, the triggering of a button on the display, or some other decisive action.

FIG. 1 is a schematic block diagram of a dialysis system 100, in which embodiments of the present inventive concepts can be practiced. In an embodiment, the dialysis system 100 includes a hemodialysis machine 104 or a related regenerative dialysis machine for performing hemodialysis or related procedures. Although a regenerative dialysis system is described, embodiments of the present inventive concepts are equally applicable to non-regenerative dialysis systems or other medical treatment devices.

During a dialysis procedure, an ECC 116 is formed between a needle 120 inserted in a body 118, where blood flows out of the body 118 through a plastic tubing 124 and into a hemodialysis machine 104. The hemodialysis machine 104 includes a dialyzer or related filtration device that removes toxins, waste, and impurities such as urea, and/or excess fluid such as water from the blood, and outputs the cleaned blood to the body 118 via a venous catheter 122. During this procedure, the ECC 116 is monitored for venous and arterial blood pressures, and for the presence of air and blood, among other monitored parameters. This cycle can be repeated as necessary during the procedure.

Also during the procedure, a dialysate circuit 114 is formed between the hemodialysis machine 104 and a dialysate system 110. The dialysate system 110 outputs dialysate mixed with purified water to the dialyzer of the hemodialysis machine 104. Toxins, waste, and the like are transferred at the dialyzer from the circulating blood to the dialysate via diffusion or osmosis occurring across a semipermeable membrane 126 at the hemodialysis machine 104. The used dialysate containing the waste is output from the hemodialysis machine 104 to a sorbent cartridge (not shown) at the dialysate system 110, which purifies the dialysate by removing the toxins, waste, and the like from the used dialysate. The purified dialysate can then be output to the hemodialysis machine 104 where the cycle can be repeated. The hemodialysis machine 104 and the dialysate system 110 can include other elements such as pumps, sensors, filters, and the like, which are well-known to those of ordinary skill in the art and will therefore not be described herein for reasons related to brevity.

Various monitors, meters, sensors, detectors, and the like are positioned along the ECC 116 and the dialysate circuit 114, including the dialysate system 110 and/or the hemodialysis machine 104, to monitor an array of safety-critical parameters prior to or during a dialysis procedure, including but not limited to blood and dialysate flow rates, temperature, arterial and venous pressure, dialysis solution conductivity, temperature, and ultrafiltration (UF) control parameters.

For example, the dialysis system 100 can include an inflow sensor 106 and an outflow sensor 108 along the dialysate circuit 114 for monitoring dialysate conductivity, temperature, UF flow rate, and so on, the results of which are output to a control panel 134 for analysis and display via event signals 138. In another example, the dialysis system 110 can include an arterial pressure monitor 130, a venous pressure monitor 132, a blood sensor 136, and related detectors along the ECC 116, which output relevant data via arrows 138 to the control panel 134 for analysis and display.

The control panel 134 includes a display and other input/output devices, such as a keypad, a touchpad, a keyboard, and/or a mouse. The display can be a monitor, touchscreen, terminal, or other visual display. The display can include a graphical user interface application or other program for generating one or more treatment display screens, windows, and the like. When multiple display screens, windows, and the like are displayed, an operator can switch or toggle between them. This can be achieved for example, by dragging, minimizing, or changing a position of one display screen or window to prominently display another display screen or window. An operator can enter treatment parameters related to a medical procedure to the dialysis system 100 via a treatment display screen using a mouse, keyboard, touchscreen interface, voice recognition device, or other input device. Dialysis-related event information can be displayed at the treatment display screen, for example, a dialysis procedure, and to monitor the dialysis system 100 for events related to a dialysis procedure and the like.

Figure 2:
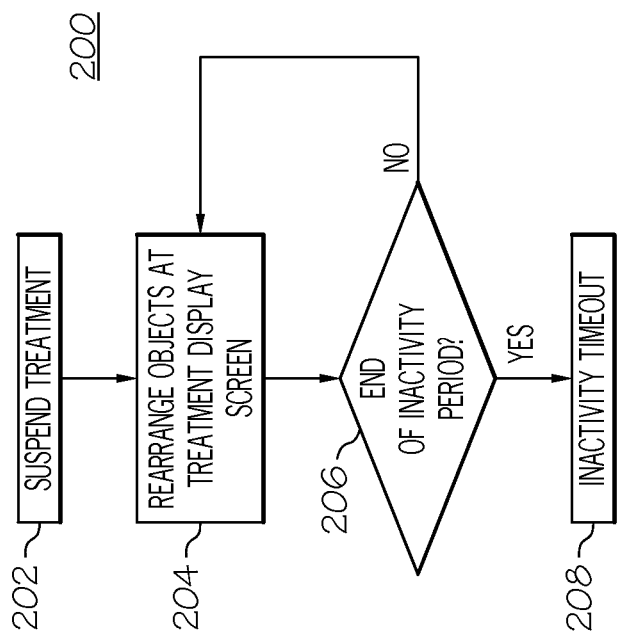
FIG. 2 is a flowchart illustrating a method for displaying parameters at a dialysis system control panel, in accordance with an embodiment.

FIG. 2 is a flowchart illustrating a method 200 for displaying parameters at a dialysis system control panel, in accordance with an embodiment. In describing the method 200, reference is also made to elements of the dialysis system 100 of FIG. 1. For example, some or all of the method 200 can be implemented at the control panel 134 described in FIG. 1.

At block 202, a medical treatment is suspended, for example, by selecting a button or other selection feature at the display screen of the control panel 134. A unique key sequence can be provided to ensure that a treatment cannot be initiated for a predetermined period of time during which objects at the treatment display screen can be rearranged.

At block 204, objects displayed at the treatment display screen, e.g., edit buttons, charts, graphs, tables, and the like are in a fluid, or movable, state, and can be rearranged. The state of the treatment display objects can automatically transition from the fluid state to a fixed state, whereby object fluidity is prevented when treatment-related events are detected. For example, treatment display objects cannot be rearranged when the treatment display screen displays the operational mode of the dialysis system 100 as being in a dialysis treatment mode. In some embodiments, object fluidity is prevented when other operation-related events are detected, for example, when the blood sensor 136 detects blood in the ECC, or when any other indicators determine that a treatment is in progress or is capable of being initiated. The treatment display screen can include two or more display screens or windows. In one embodiment, one or more treatment display objects on a first display screen or window are interchanged with treatment display objects on a second display screen or window in accordance with the systems and methods described herein. In another embodiment, one or more treatment display objects on a first display screen or window are rearranged on another display screen or window in accordance with the systems and methods described herein.

At decision block 206, a determination is made whether no activity occurs with respect to the rearrangement of treatment display objects for a predetermined period of time, referred to as an inactivity timeout period. If no activity occurs during the inactivity period, than at block 208, an inactivity timeout signal is generated, in response to which the treatment display screen objects transition from a fluid state to a fixed state. This ensures that machine efficacy is maintained. Here, an operator can be permitted to perform a dialysis procedure and the like, for example, using the newly defined object arrangement.

Figure 3:
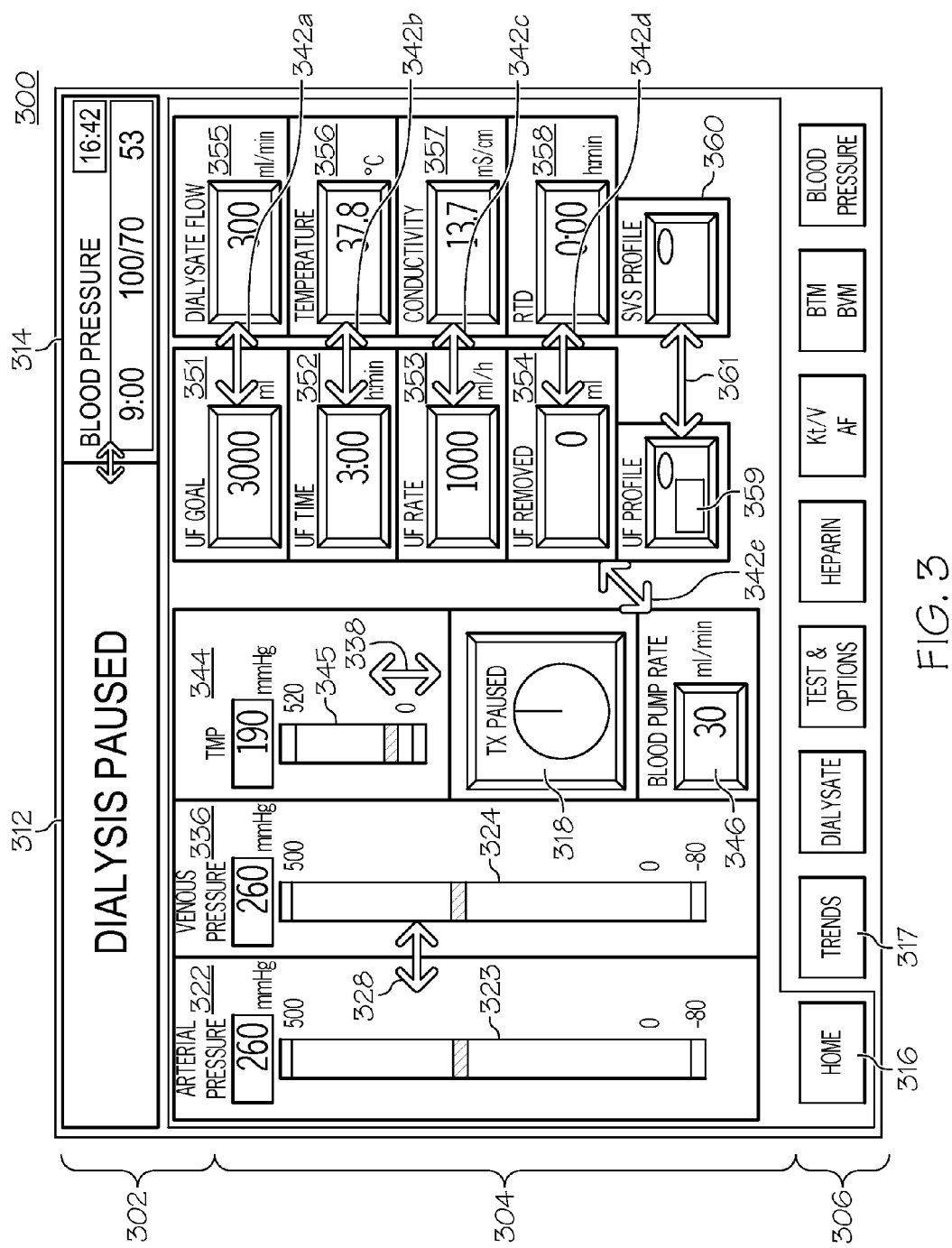
FIG. 3 is a screenshot of a treatment display screen, in accordance with an embodiment.

FIG. 3 is a screenshot of a treatment display screen 300, in accordance with an embodiment. The treatment display screen 300 is used to access and set treatment parameters related to medical procedures such as a dialysis procedure. The treatment display screen 300 corresponds to a home screen, for example, selected by pressing, or otherwise triggering, a screen button 306, in particular, a Home button 316, or a Trends button 317.

In some embodiments, multiple screens, windows, and the like, are simultaneously displayed at the treatment display screen 300, where an object of one screen can be moved to another screen and added to an existing set of objects at the other screen. Alternatively, two or more objects on different displayed screens can be interchanged with each other.

The treatment display screen 300 comprises a status section 302, a treatment display window 304, also referred to as a treatment display section, and the abovementioned screen buttons 306, also referred to as treatment display keys.

The status section 302 includes a status box 312 and a dialog box 314, which display notification information during an operation performed by the hemodialysis machine 104. The status box 312 displays the operational mode of the machine, for example, a dialysis mode, indicating that a dialysis operation is in progress, or a dialysis paused mode, indicating that a dialysis procedure is suspended or prevented from being initiated. The dialog box 314 displays information such as blood pressure readings. When an abnormal event occurs, for example, a particular treatment parameter falls outside a predetermined range, or an operator enters an unacceptable parameter value, the status box 312 and/or the dialog box 314 can display a notification corresponding to the event. For example, the dialog box 314 can display a message notifying the operator that an incorrect parameter value was entered by the operator. In another example, the status box 312 can display an alarm or a warning, for example, a low temperature alarm, generated when a detector, monitor, and the like detects an abnormal event. In some embodiments, the operation of the status section 302 can be performed according to the systems and methods described in U.S. patent application Ser. No. 13/299,790, entitled "Systems and Methods for Providing Notifications in Dialysis Systems," the contents of which are incorporated by reference herein in their entirety.

The treatment display window 304, also referred to as a treatment display section, includes one or more regions for viewing various treatment data, for example, an arterial pressure display region 322 that includes a value field, e.g., displaying an arterial pressure value of 260 mmHg, and a corresponding vertical bar graph 323 for graphically displaying the arterial pressure value. Also, a venous pressure display region 336 includes a value field, e.g., displaying a venous pressure value of 260 mmHg, and a corresponding vertical bar graph 324 for graphically displaying the venous pressure value. The treatment display window 304 also includes a plurality of data buttons or other objects, in particular, treatment parameter buttons, that an operator can set, for example, treatment parameters related to ultrafiltration rate, dialysate conductivity levels, and the like. For example, as shown in FIG. 3, an operator can enter a UF goal value of "3000" at an edit button 351 entitled "UF Goal" to set the UF Goal for treatment to be 3000 ml.

The treatment display window 304 includes a treatment clock button 318. During treatment, the treatment clock button 318 can display a "Tx Running" message (not shown). When treatment is suspended, for example, by pressing the treatment clock button 318, the treatment clock button 318 can display a "Tx Paused" message as shown. A corresponding advisory message "Dialysis Paused" can appear at the status box 312 when treatment is suspended.

The screen buttons 306 permit an operator to access and view the various treatment display screens displayed at the treatment display window 304. For example, as shown in FIG. 3, a treatment display screen can include a home screen that is displayed by selecting the Home screen button 316. Although a home treatment display screen is shown and described herein, other display screens can be displayed, depending on the screen button 306 that is selected. For example, a trends screen (not shown) can display one or more graphs depicting various treatment progress indicators by pressing a Trends button 317.

The objects of the regions displayed at the treatment display window 304, for example, the data buttons, graphs, and so on, and/or the screen buttons 306, can be configured to be in a fluid state, where the buttons and the like can be rearranged at the treatment display screen 300 when treatment is disabled, is suspended, or is otherwise not in progress, i.e., when the treatment clock button 318 displays a "Tx Paused" message. Here, arrows or other indicators can be displayed that identify potential destination locations on the treatment display screen 300 for moving a selected object. For example, arrow 328 is displayed between the arterial pressure display region 322 including the bar graph 323 and the venous pressure display region 336 including the bar graph 324, indicating that display regions 322, 336 can be interchanged in a horizontal direction with respect to each other. Likewise, arrows 342a-342d displayed between the parameter buttons display regions 351-358 indicate that these display regions can be interchanged horizontally and/or vertically with respect to each other. Lastly, arrow 342e displayed between the parameter buttons 346 and 351 indicate that these display regions can be interchanged diagonally with respect to each other.

In another example, arrow 338 is displayed between the treatment clock button 318 and a transmembrane pressure display region 344 including a bar graph 345, indicating that the treatment clock button 318 can be relocated to the transmembrane pressure display region 344, or a region directly adjacent the transmembrane pressure display region 344, or that the treatment clock button 318 and the transmembrane pressure display region 344 can be interchanged in a vertical direction.

In another example, arrow 342e is displayed between a Blood Pump Rate edit button 346 and a UF Removed edit button 354, indicating that the Blood Pump Rate edit button 346 and a UF Removed edit button 354 can be interchanged in a diagonal direction. Additionally, relocating the Blood Pump Rate edit button 346 with respect to any of the other parameter buttons, for example, above the UF Rate edit button 353, can result in the UF Removed edit button 354 moving diagonally downward to the display region originally displaying the Blood Pump Rate edit button 346.

In another example, arrow 342a is displayed between the UF Goal edit button 351 and a Dialysate Flow edit button 355, indicating that the UF Goal edit button 351 and the Dialysate Flow edit button 355 can be interchanged in a horizontal direction.

In another example, arrow 342b is displayed between the UF Time edit button 352 and a Temperature edit button 356, indicating that the UF Time edit button 352 and the Temperature edit button 356 can be interchanged in a horizontal direction.

In another example, arrow 342c is displayed between the UF Rate edit button 353 and a Conductivity edit button 357, indicating that the UF Rate edit button 353 and a Conductivity edit button 357 can be interchanged in a horizontal direction.

In another example, arrow 342d is displayed between the UF Removed edit button 354 and the RTD edit button 358, indicating that the UF Removed edit button 354 and the RTD edit button 358 can be interchanged in a horizontal direction.

In another example, arrow 342e is displayed between the UF Removed edit button 354 and the Blood Pump Rate edit button 346, indicating that the UF Removed edit button 354 and the Blood Pump Rate edit button 346 can be interchanged in a diagonal direction.

In another example, arrow 361 is displayed between a UF Profile button 359 and an SVS Profile button 360, indicating that the UF Profile button 359 and the SVS Profile button 360 can be interchanged in a horizontal direction.

In some embodiments, the treatment clock button 318 is disabled, or otherwise prevented from being engaged to initiate a treatment when the treatment display objects are in a fluid state and configured for rearrangement on the treatment display screen. Since the treatment clock button 318 can be the primary control interface for an operator to initiate a treatment, disabling the button 318 on the screen during an object arrangement is an effective way to prevent activation or re-activation of a treatment during this reconfiguration.

Embodiments of the present inventive concepts can also provide additional safeguards to ensure that an operator does not accidentally perform such a rearrangement during a treatment whereby patient safety can be otherwise compromised; such as the safeguards described herein.

Figure 4:
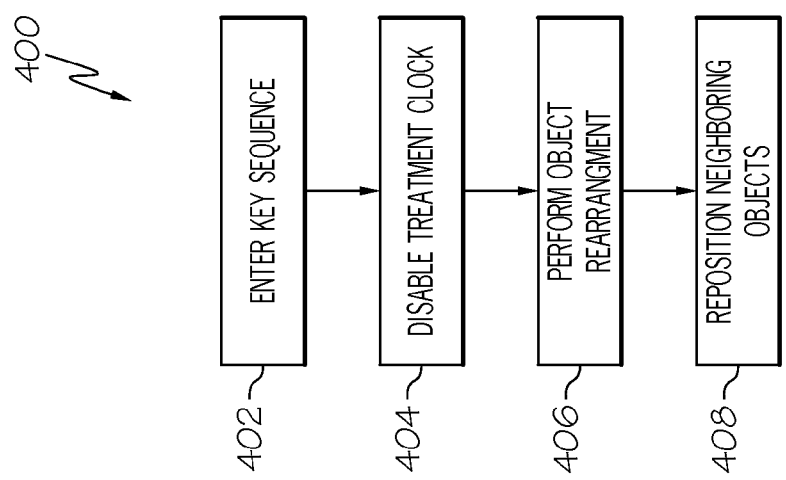
FIG. 4 is a flowchart illustrating a method for preventing a medical treatment from being performed when treatment display objects are in a fluid state, in accordance with an embodiment.

FIG. 4 is a flowchart illustrating a method 400 for preventing a medical treatment from being performed when treatment display objects are in a fluid state, in accordance with an embodiment. In describing the method 400, reference is also made to elements of the dialysis system 100 of FIG. 1 and/or the treatment display screen 300 of FIG. 3. For example, some or all of the method 400 can be implemented at the control panel 134 described in FIG. 1. In another example, the rearrangement of objects described with respect to FIG. 3 can be performed according to the method 400.

At block 402, a key sequence can be entered at the control panel 134 for allowing treatment display objects such as buttons to be rearranged at the treatment display screen 300. The key sequence can include letters or other characters entered into a field (not shown) at a display screen presented at the control panel 134, similar to a password. Alternatively, the key sequence can be entered via special control panel keys, for example, using a keypad (not shown) in communication with the control panel 134.

At block 404, the treatment clock is disabled, for example, by inactivating the treatment clock button 318. In this manner, a dialysis procedure cannot be initiated, regardless of whether an operator presses the treatment clock button 318. The treatment clock button 318 can display a "Tx Paused" message, or a related message such as a "Tx Disabled" message, during a predetermined period during which the treatment clock is disabled.

At block 406, a rearrangement of objects such as buttons, charts, and the like can be performed by the operator. For example, during an object rearrangement operation, the arterial pressure bar graph 323 and the venous pressure bar graph 324 shown in FIG. 3 can be interchanged with each other, or otherwise rearranged on the treatment display screen 300.

In an embodiment, referring to FIG. 2, a period of inactivity can be detected within the predetermined period during which the treatment clock is disabled, for example, when no rearrangement occurs by the operator. An inactivity timeout parameter can be implemented which changes the state of the treatment display objects from a fluid state, wherein rearrangement is permitted, to a fixed state, for example, at a time when the period of inactivity exceeds the predetermined period. The treatment clock can thereafter be enabled when the treatment display objects return to the fixed state. Upon return to the fixed state, an operator can select the treatment clock button 318 to initialize or resume a treatment.

At block 408, neighboring objects at the second location surrounding the newly relocated object can be repositioned so that the selected object does not overlap or obscure the neighboring objects. Arrows or other indicators can illustrate to the operator how the surrounding objects are impacted when the newly relocated object is moved to the second location.

Figure 5:
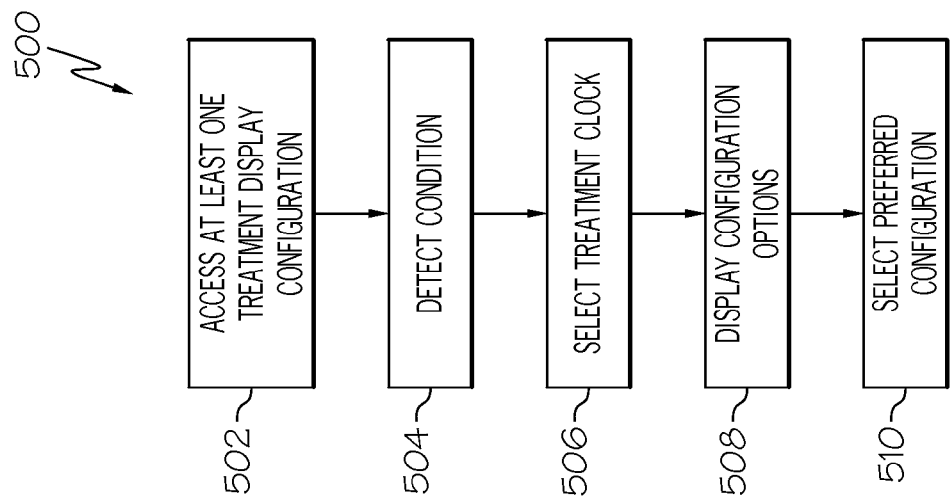
FIG. 5 is a flowchart illustrating a method for activating a treatment display screen configuration, in accordance with an embodiment.
Figure 6:
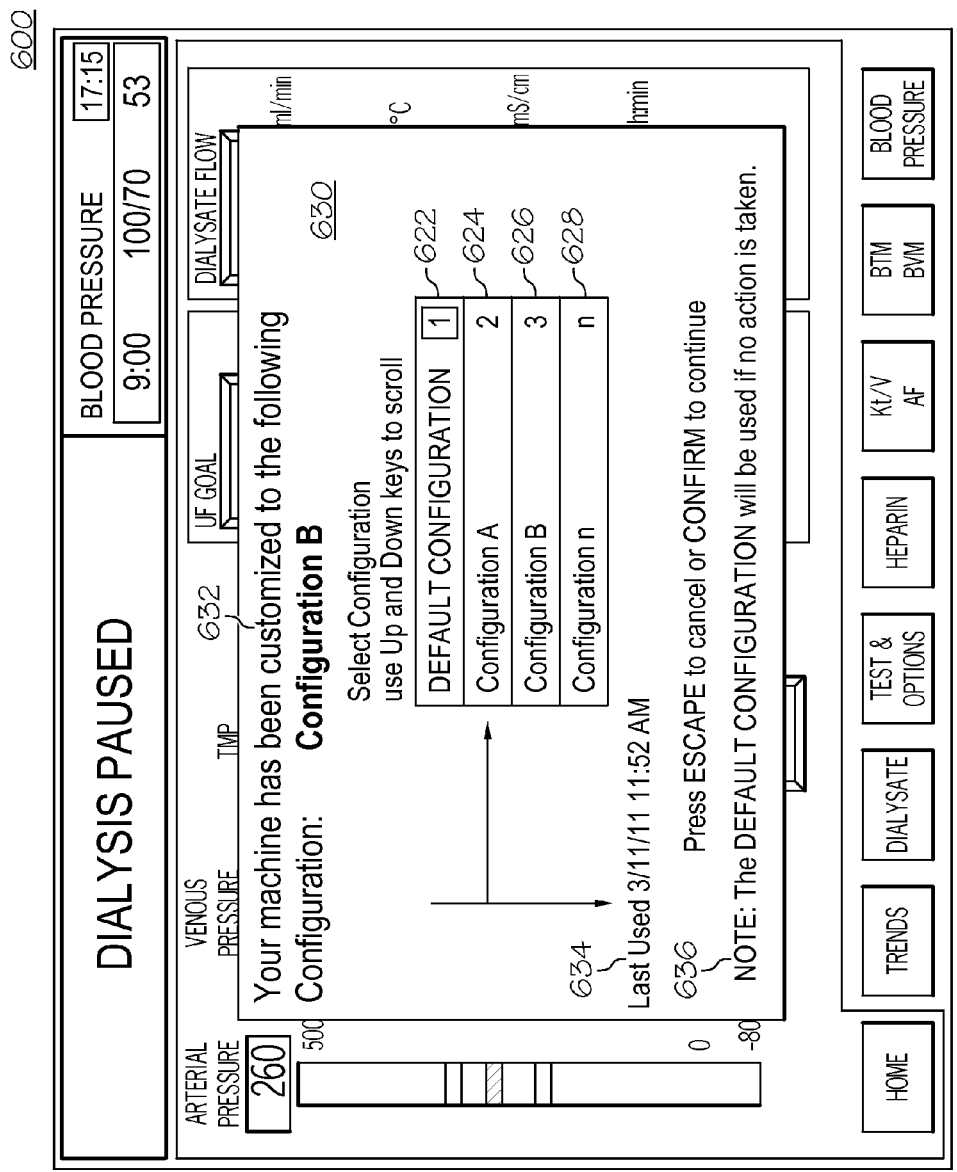
FIG. 6 is a screenshot of a treatment display screen displaying a set of configuration options, in accordance with an embodiment.

FIG. 5 is a flowchart illustrating a method 500 for activating a treatment display screen configuration, in accordance with an embodiment. In describing the method 500, reference is also made to elements of the dialysis system 100 of FIG. 1. For example, some or all of the method 500 can be implemented at the control panel 134 described in FIG. 1. FIG. 6 is a screenshot of a treatment display screen 600 displaying a set of configuration options in accordance with the method 500. Accordingly, in describing the method 500, reference is also made to elements of the treatment display screen 600.

At block 502, an operator can access a listing of options with respect to different treatment display screen configurations 622, 624, 626, 628 to the control panel 134. Each configuration can include a different arrangement of objects on the treatment display screen 600. For example, an operator can provide a first configuration 624, also referred to as Configuration A. One example of a unique configuration can be the arrangement of the contents of the treatment display screen 300 shown in FIG. 3. The operator can form a second configuration 626 of the treatment screen 300, also referred to as Configuration B, by rearranging objects of the treatment display screen 300 according to the methods described herein. Each time an operator identifies a desired configuration during a rearrangement of objects at the treatment display screen 300, an operator can save the configuration, for example, by entering a key sequence or by selecting a save button that is presented at the display 300 at the end of a predetermined period of time when the objects are in a fluid state. For example, the first configuration 624 and the second configuration 626 can be saved by an operator, and stored in a memory device, for example, the configuration repository 1008 described with reference to FIG. 10.

A default configuration 622 can also be stored in the memory device. The default configuration 622 can be hardcoded, for example, generated automatically at the control panel 134 according to a configuration provided by the manufacturer of the dialysis system 100 such as an "out-of-the-box" configuration.

At block 504, a change in the condition of the dialysis system 100 is detected. This can include a failure related to the hemodialysis machine 104, a system power down, a power failure, and the like. Other conditions can include a new treatment or a reinitialization of a treatment clock button at the control panel 134. After the condition occurs, the treatment clock button is first presented. The treatment clock button can be similar to the treatment clock button described with respect to FIGS. 2-4. The treatment clock button is displayed at the treatment display screen 600 but is not shown in FIG. 6 because it is obscured by a reminder window 630, described below, which is subsequently displayed on the treatment display screen 600. Accordingly, at block 506, the treatment clock button can be selected by an operator, for example, by pressing a region of a touchscreen displaying the treatment clock button, or by using a mouse to move a cursor over the treatment clock button, or by applying a related technique known to those of ordinary skill in the art.

Each configuration 624, 626, 628 can correspond to an arrangement of objects corresponding to a unique operator. For example, Configuration A 624 can include an arrangement of objects preferable to a nurse, while Configuration B 626 can include an arrangement of objects preferable to a patient.

At block 508, the reminder window 630 is generated in response to an event such as a power failure, treatment re-initialization, and the like, and further in response to an activation of the treatment clock. The reminder window 630 includes a set of available configuration options. The reminder window 630 can be displayed in response to a change in condition of the dialysis system 100 as described in the method 600. In other embodiments, the reminder window 630 is presented when the current configuration is determined to be undesirable, for example, if a new patient or nurse finds the current configuration to be undesirable. The reminder window 330 is displayed to provide other configuration options, for example, Configuration B, for an operator to select from when a current configuration, for example, Configuration A, is deemed undesirable. In some embodiments, a suggested configuration can be indicated, for example, as suggested in response to historical information stored in the configuration repository 1008. Alternatively, the hemodialysis machine 104 can automatically revert to the default display screen configuration 622.

The reminder window 630 can include a reminder message 632 that is displayed indicating a current configuration, i.e., Configuration A. The reminder window 630 can also display a message 634 that displays information regarding a recently executed configuration, for example, a time and date that the current configuration, Configuration A, was last used. Other configurations can also be identified, for example, the most popular or most used configuration.

At block 510, a configuration can be selected among the configuration options 622, 624, 626, and 628, for example, by selecting a key. The control panel 134 can be configured to automatically revert to the default configuration 622 if no action is taken. A message 636 can be displayed at the control panel 134 providing this information to a viewer such as the operator.

Figure 7:
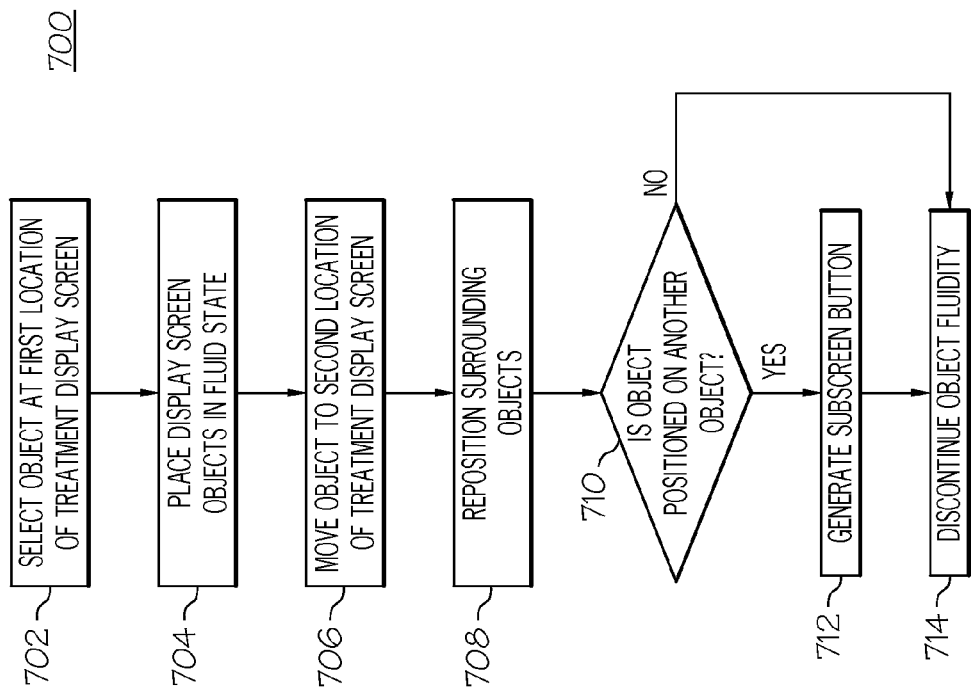
FIG. 7 is a flowchart illustrating a method for rearranging objects on a treatment display, in accordance with an embodiment.

FIG. 7 is a flowchart illustrating a method 700 of rearranging objects on a treatment display screen, in accordance with an embodiment. In describing the method 700, reference is also made to elements of FIGS. 1-6. Some or all of the method 700 can be implemented, for example, in the control panel 134 described in FIG. 1, and applied to the treatment display screen 300 shown and described with reference to FIG. 3.

At block 702, an object is selected at a first location of the treatment display screen. The object can be a discrete object that is displayed as a button, icon, window, graph, or other display image. The treatment display screen is presented at the dialysis system control panel 134, or other terminal, monitor, touchscreen, and the like used in performing medical treatments. The object can be selected by positioning a mouse cursor over the selected object or by applying physical pressure to the location at the treatment display screen, for example, at a touchscreen, or by performing other well-known techniques for moving displayed objects such as voice recognition or other suitable techniques.

At block 704, the treatment display screen objects can be placed in a fluid state, permitting the displayed objects to be moved to different regions of the treatment display screen. Here, a rearrangeement mode of operation can be activated at the treatment display screen. Some or all of the objects at the treatment display screen can be unlocked, i.e., changed from a fixed state to a fluid state, by entering a special key or other unlock sequence or related security feature at the control panel 134. In some embodiments, a subset of the objects can be placed in a fluid state. A window, edit button, or other field can be displayed at the treatment display screen for entering characters and the like that comprise the special key or unlock sequence. In response to an activation of the rearrangement mode of operation, selected objects can be rearranged at the treatment display screen, for example, moved to another location of the treatment display screen, or interchanged with a button, graph, or other object. Starting the treatment clock is prevented during operation in the rearrangement mode so that a medical treatment cannot be initiated or otherwise performed while the objects are in a fluid state.

At block 706, the selected object, after being unlocked, can be moved to a second location of the treatment display screen. During repositioning to the second location, the object can be modified to be visually distinct from neighboring objects, for example, enlarged. The operator can receive instructions where to move the object, for example, visually guided by arrows or other indicators that identify potential destination locations on the treatment display screen for the selected object.

At decision block 708, a determination is made as to whether the displayed selected object is positioned on top of or proximal to another displayed object. If yes, then at block 710, a corresponding subscreen button can be created. Here, a blank field can be provided for the operator to enter the name of the subscreen button. The subscreen button can include an object repository that includes both the selected object and the other displayed object. Other contents such as additional objects can be added to the object repository.

At block 712, object fluidity can be discontinued after performing the operation at block 710, or if a determination is made at decision block 708 that the displayed object is not positioned on top of another displayed object. A dialog message can appear at the treatment display screen to confirm whether the operator has completed changes made to the treatment display screen. Here, the operator can select a Confirm key and the like to confirm that all changes have been made. Accordingly, the treatment clock can subsequently be activated, giving the operator the ability to initiate a medical treatment.

Figure 8:
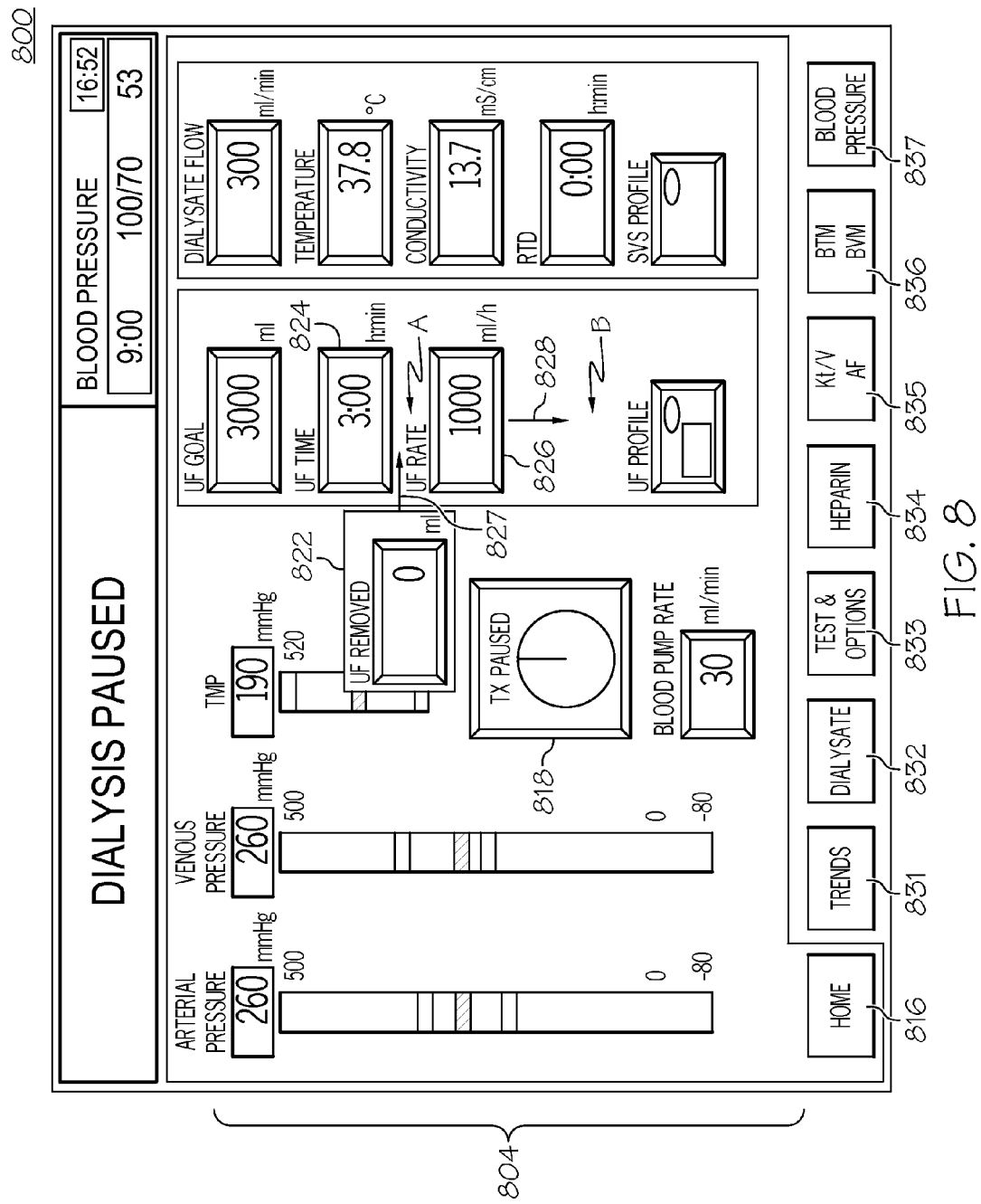
FIG. 8 is a screenshot of a treatment display screen displaying the movement of an object at a treatment display, in accordance with an embodiment.

FIG. 8 is a screenshot of a UF Removed button 822 and a UF Rate button 826 being moved on a treatment display screen 800. Vertical repositioning of the UF Removed button 822 and the UF Rate button 826 can occur relative to their positions shown in FIG. 3. Various features of the treatment display screen 300 described herein with respect to FIG. 3 can equally apply to the treatment display screen 800 and will therefore not be repeated for the sake of brevity. The treatment display screen 800 can be displayed by selecting a Home screen button 816. However, the systems and methods of the embodiments described herein can apply to other display screens, for example, a Trends screen (not shown) displaying graphs when a Trends screen button 831 is selected, or other screens when one or more other buttons 832-837 are selected.

A treatment display window 804 is presented at the treatment display screen 800. Here, an operator or other user can select the UF Removed button 822 when the button 822 is in a fluid state, and move the button 822 to a different location of the treatment display screen 800. A special key sequence or other activation feature can be generated to change the UF Removed button 822 from a fixed state to a fluid state. The treatment clock button 818 can display a "Tx Paused" status message, or similar message, indicating that no dialysis treatment is currently being performed. The treatment clock button 818 cannot be activated, i.e., changed to a "Tx Running" status, and therefore, a treatment cannot be initiated, while the button 822 is in the fluid state.

A first arrow 827 can be displayed when the user begins to move the button 822 to a different location to illustrate a possible location for the button 822, for example, location A between the UF Time button 824 and the UF Rate button 826. A second arrow 828 can also be displayed to indicate the subsequent impact on surrounding objects upon placement of the button 822 at location A. For example, arrow 828 can be displayed to show that the UF Rate button 826 is in a region proximal to the possible destination location A of the UF Removed button 822, and will be moved to location B if the UF Removed button 622 is moved to location A.

As the button 822 is moved about the treatment display screen 800, the arrows can change, or continuously refresh to indicate new locations of the button 822 and other display objects that will be affected by a relocation of the button 822. In some embodiments, the displayed arrows can correspond to system-recommended repositioning of the objects. For example, such recommendations can be based on predetermined judgments of correlation of the objects to ensure the objects' proximity to each other. In some embodiments, such recommendations can be based on patient safety. In some embodiments, the arrow recommendations can be overridden by the operator in response to an operator input. In some embodiments, the arrow recommendations are not presented on the display, whereby the objects can be relocated at any region of the treatment display screen without constraint, for example, in a "free-form" format.

After the button 822 is moved to location A, and after it is determined that the button rearrangement is completed, the display can be returned to a fixed mode from the fluid mode. Following the return to a fixed mode, the treatment clock button 818 and/or special key sequence, e.g., Confirm key, can be activated so that a dialysis procedure and the like can be performed.

In an embodiment, the treatment display screen 800 is arranged as an N×M display matrix, where N refers to a number of rows and M refers to a number of columns. Each displayed object can be located in a cell defined by a particular row and a particular column. When an object is moved from an original location of the display matrix, e.g., a first cell, to a new location of the display matrix, e.g., a second cell, a vacancy is created at the original location of the display matrix. The vacancy can be populated with one or more other displayed objects according to the following approach.

The column and row of the original location and the new location of the object are determined. The relationship is determined between the original location and the new location of the object. For example, a determination can be made that the original location, e.g., the first cell, of the object is a predetermined number of rows and/or columns from the new location, e.g., the second cell, of the object. If the new location of the object at the display matrix is at a column located to the left of the column of the original location, then one or more objects adjacent the newly created vacant first cell are moved to the right of the treatment display screen to fill the vacant region, i.e., the first cell, at which the object was originally located. Accordingly, the vacant region is shifted, column by column, to the second cell at which the object is to be relocated. A vacant region is then formed at the second cell, since an object previously occupying the second cell is shifted to a different cell located to the right of the second cell. The object can be positioned at the newly vacant second cell.

In another embodiment, the new location of the object at the display matrix is at a column located to the right of the column of the object's original location. Here, one or more objects adjacent the newly located object are moved to the left of the treatment display screen to fill the vacant region at which the object was originally located. Accordingly, the vacant region is shifted in a direction to the right of the original location, column by column, until the vacant region is positioned at the cell at which the object is to be relocated. The object can be positioned at the newly vacant cell.

In another embodiment, the new location of the object at the display matrix is at a row located above the cell at which the object is originally positioned. An example is illustrated at FIG. 8, where the UF Removed button 822 is moved to a location A. The UF Removed button 822 and the UF Rate button 826 are at the same column of the display matrix. However, the destination location A is located at a higher row of the display matrix than the row of the original location of the UF Removed button 822, i.e., location B. Here, the adjacent object, i.e., the UF Rate button 826, is moved down in the treatment display screen 800 to fill the vacant region at location B at which the UF Removed button 822 was originally located, permitting the UF Removed button 822 to be positioned at the newly vacant region at location A. In another embodiment, objects can be rearranged in a similar manner when the new location of an object is at a row below its original location.

In the embodiments described above, an object is moved to a different row or a different column of a treatment display screen. In other embodiments, the approaches described above can equally apply to objects that are moved to a different row and a different column, for example, from a lower left location of a treatment display screen to an upper right location of the treatment display screen.

In other embodiments, no objects are directly adjacent, for example, above or to the side of, a newly vacated region previously occupied by an object that is moved to a different location of a treatment display screen. Therefore, the vacated region cannot be populated by an object directly adjacent the vacated region. Here, an object that is diagonal the vacated region can be relocated to the vacated region. The abovementioned approaches with respect to moving objects up, down, left, or right, can be applied to populate the region previously occupied by the diagonal object. In another embodiment, any objects that cannot be moved to another location of a treatment display screen, for example, due to the inability to create a vacant location for an object to be relocated, can be prevented from entering a fluid state from a fixed state. This can be achieved by inactivating a rearrangement mode of operation of the treatment display screen.

FIGS. 9A-9D are screenshots illustrating the formation of a subscreen by merging objects on a treatment display screen 900, in accordance with an embodiment. This can be achieved by implementing some or all of the method 700 in the control panel 134 described in FIG. 1. In some embodiments, the merger of the objects can correspond to a merger or grouping of objects of common data parameters or common themes into a folder object or sub-screen object. As shown in FIGS. 9A-9D, in some embodiments, the objects can be parameter or edit buttons. The objects can alternatively take the form of bar graphs, charts, and the like. The objects can be rearranged at the treatment display screen 900. Two or more objects of the same type can be merged with each other. For example, a UF Rate button 928 and a UF Time button 924 can be merged as shown.

Figure 9A:
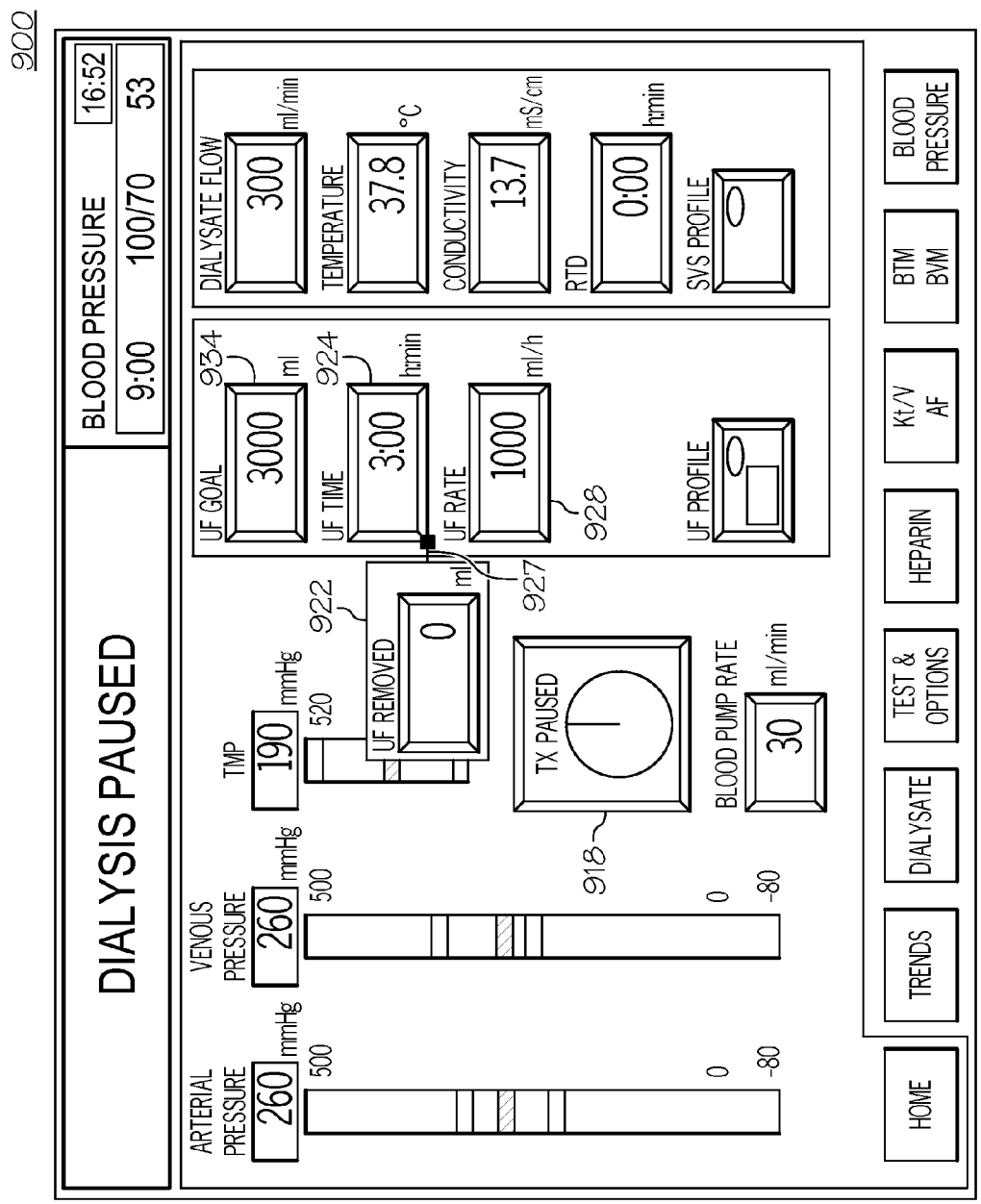
FIGS. 9A-9D are screenshots illustrating a method for creating a subscreen by merging objects on a treatment display, in accordance with an embodiment.

In FIG. 9A, the display is changed from a fixed state to a fluid state in accordance with embodiments described herein. During movement of the UF Removed button 922, a connector 927 is displayed between the UF Removed button 922 and the UF Time button 924, providing an indication to an operator that the UF Removed button 922 can be positioned over the UF Time button 924, and that the UF Removed button 922 and the UF Time button 924 can be grouped together under a subfolder.

Figure 9B:
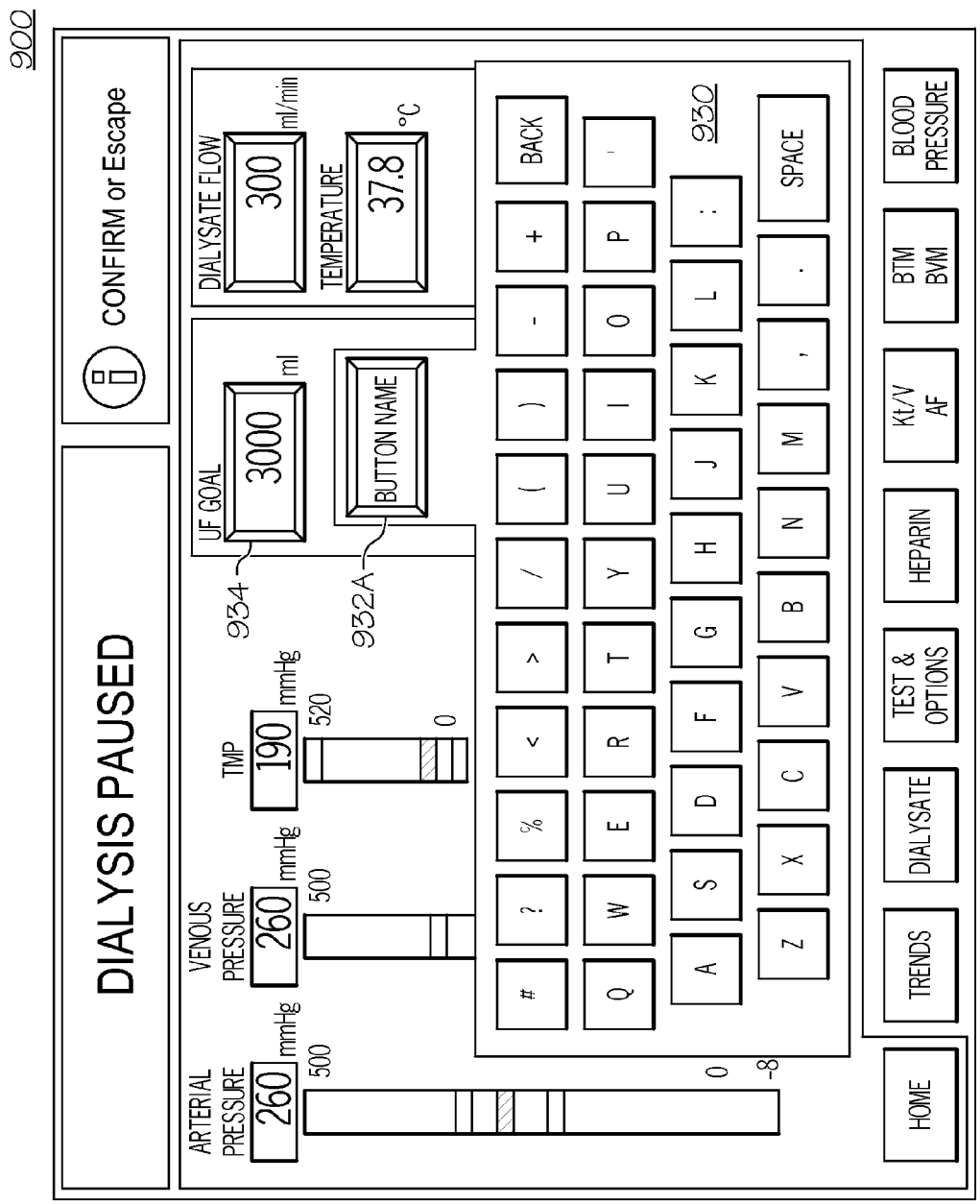
Figure 9C:
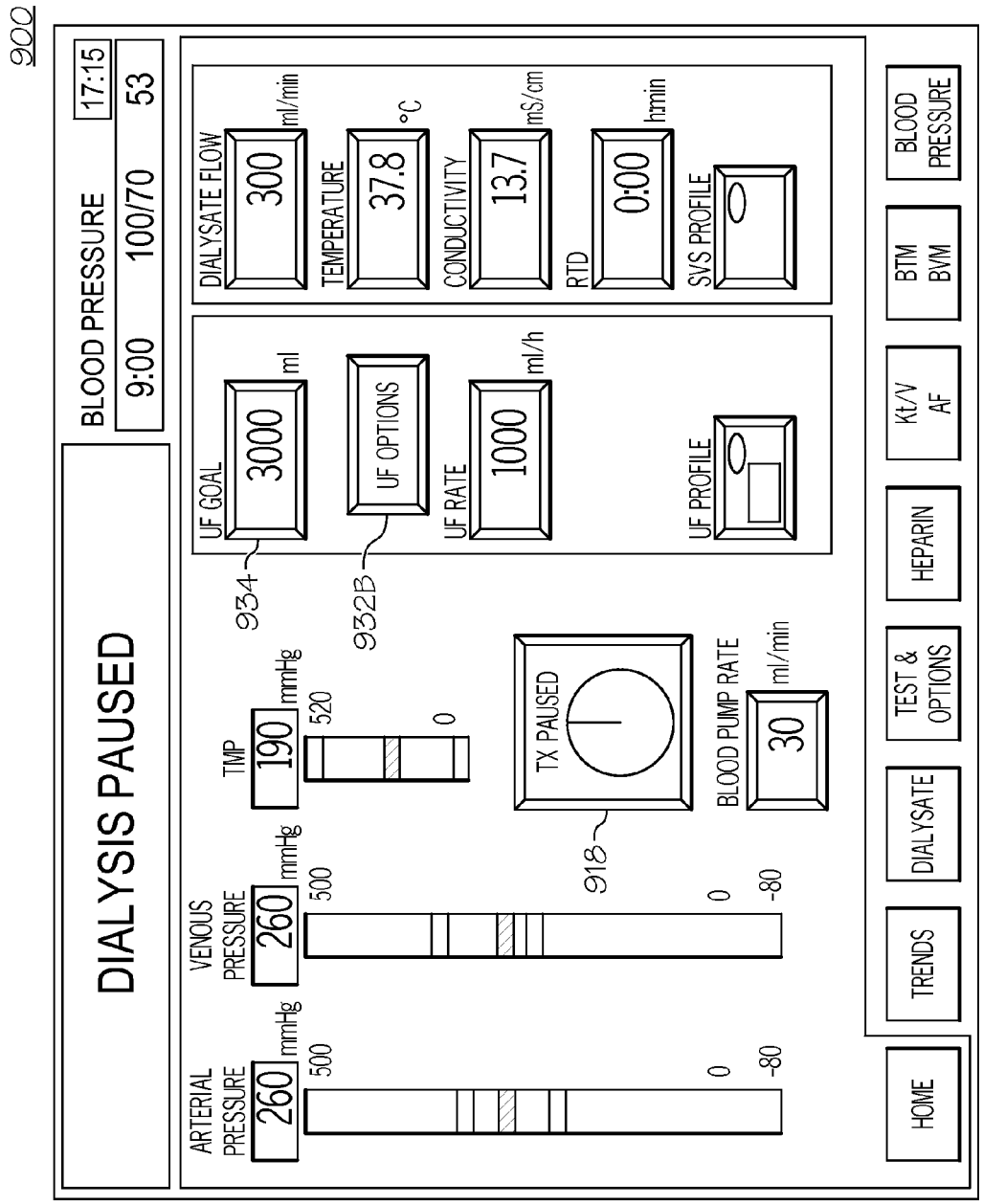

In FIG. 9B, a subscreen button editing screen 930 is presented at the treatment display screen 900 when the UF Removed button 922 is placed for merger over the UF Time button 924 on the treatment display screen 900. The screen 930 can include a virtual keyboard, permitting a user to enter data, commands, or other inputs to an application executed by a processor at the control panel 134. Alternatively, a standalone keyboard, keypad, voice recognition interface, and the like can be in communication with the screen 930 for entering data and the like. An editable button 932A is also displayed. The virtual keyboard can be used to rename the button 932A. For example, a user can enter letters, numbers, or other characters in the field 932B using the keyboard to create a subscreen button 932B entitled "UF Options," as shown in FIG. 9C.

Figure 9D:
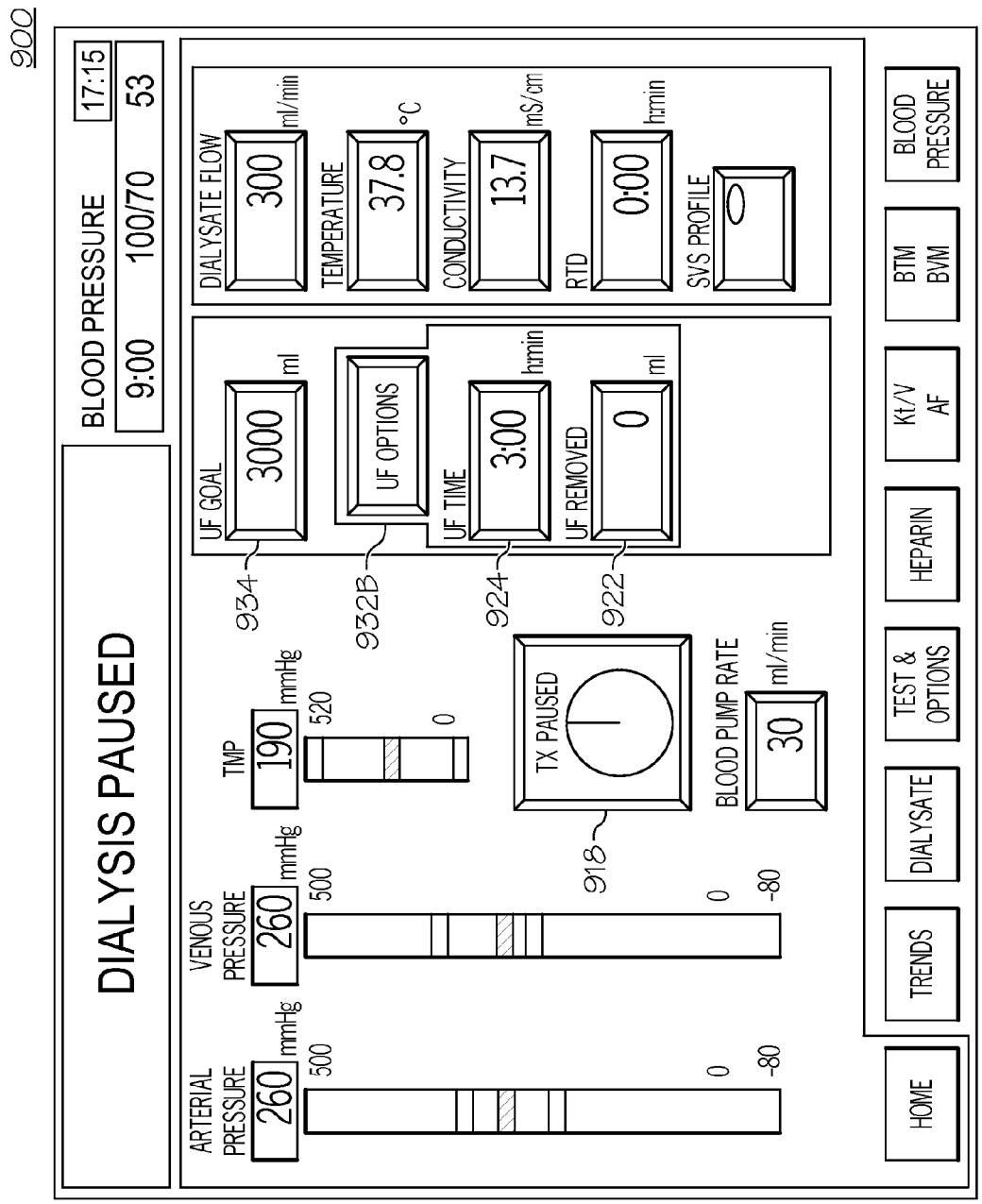

In FIG. 9D, the UF Options subscreen button 932B can be selected, wherein contents of the subscreen button 932B can be displayed, namely, the UF Time button 924 and the UF removed button 922. Other objects can be added under the subscreen button 932B, for example, the UF Goal button 934. After the subscreen button 932B is created, and after it is determined that the button rearrangement is completed, the display can be returned to a fixed mode from the fixed mode. Following the return to a fixed mode, the treatment clock button 918 and/or special key sequence, e.g., Confirm key, can be activated so that a dialysis procedure and the like can be performed.

In some embodiments, such selection and display of the subscreen button 932B can be enabled to be performed during a treatment application. In some embodiments, such selection and display of the subscreen button 932B can be disabled during a treatment operation.

Figure 10:
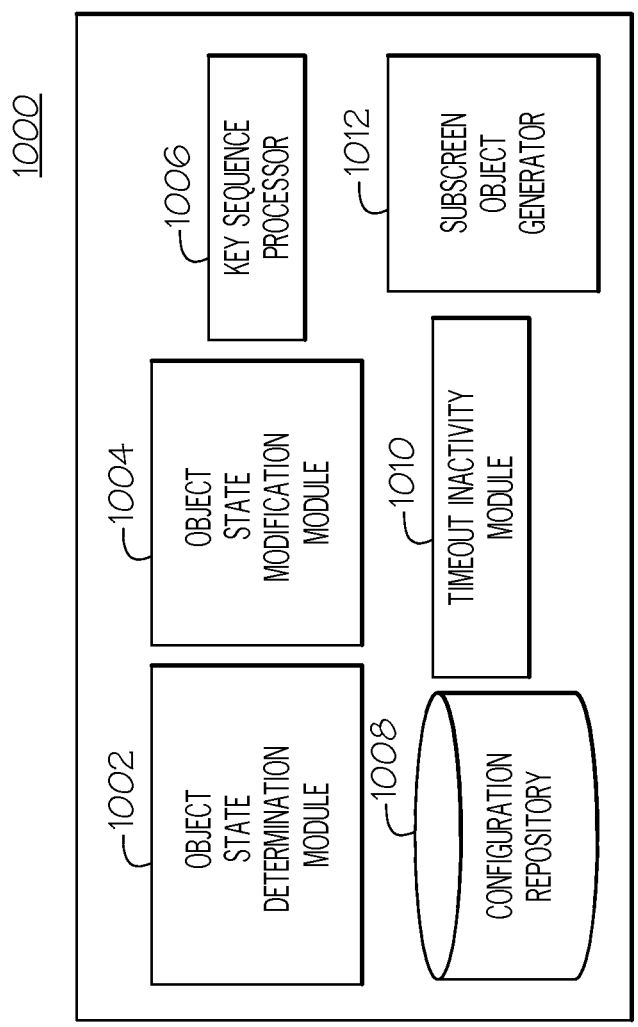
FIG. 10 is a block diagram of a display object configuration system, in accordance with an embodiment.

FIG. 10 is a block diagram of a display object configuration system 1000, in accordance with an embodiment. Some or all operations related to the systems and methods described herein can be performed at the display object configuration system 1000. The display object configuration system 1000 includes a plurality of computation units or modules that can be implemented at any of a number of different configurations, depending on the desired architecture. For example, the computation units can comprise software modules that operate on, or in connection with, one or more processors, and/or other firmware or hardware. The display object configuration system 1000 can be part of the control panel 134 described herein. Alternatively, the display object configuration system 1000 can be separate from, and in communication with the control panel 134, the hemodialysis machine 104, and/or other medical apparatus elements known to those of ordinary skill in the art.

The display object configuration system 1000 in accordance with the present embodiment comprises an object state determination module 1002, an object state modification module 1004, a key sequence processor 1006, a configuration repository 1008, a timeout inactivity module 1010, and a subscreen object generator 1012, which can communicate with each other via a bus and/or data connector (not shown), for example, a peripheral component interconnect (PCI) bus.

The object state determination module 1002 receives a signal from one or more treatment display screen objects and establishes from the signal a current state of the objects. In particular, the object state determination module 1002 establishes whether the screen objects are in a fixed state or a fluid state.

The object state modification module 1004 is configured to change the state of the screen objects from a fixed state to a fluid state and vice-versa by activating a rearrangement mode of operation of the treatment display screen. The object state modification module 1004 can receive a special key sequence or other operator entry at a user interface at the control panel 134 that is processed by the key sequence processor 1006, and in response, change the state of displayed treatment display screen objects from a fixed state to a fluid state, so that the objects can be rearranged at the treatment display screen. In some embodiments, the displayed treatment display screen objects can return from a fluid state to a fixed state, so that a treatment can be initiated or resumed.

The timeout inactivity module 1010 tracks a period of time during which the screen objects are in a fluid state. During this period of time, the objects can be rearranged at a treatment display screen. Also during this period of time, a medical treatment cannot be initiated or performed from the control display 134. Here, the timeout inactivity module 1010 can generate a signal that inactivates a treatment clock button at the treatment display screen.

The configuration repository 1008 can store treatment display screen configurations. For example, a first operator can rearrange objects on a treatment display screen according to one screen configuration. A second operator can rearrange these objects according to a different screen configuration. Each screen configuration can be stored at the configuration repository 1008 for future retrieval and activation by an operator. The configuration repository 1008 can include volatile memory, for example, RAM and the like, and/or non-volatile memory, for example, ROM, flash memory, and the like. The memory can include removable and/or non-removable storage media implemented in accordance with methods and technologies known to those of ordinary skill in the art for storing data. Stored in the memory can include program code, such as program code of an operating system, applications, or other modules described herein that can be executed by a processor.

The subscreen object generator 1012 provides a subscreen according to the method 700 at FIG. 7 and illustrated at FIGS. 9A-9D.

As will be appreciated by one skilled in the art, aspects of the present inventive concepts may be embodied as a system, method or computer program product. Accordingly, aspects of the present inventive concepts may take the form of an entirely hardware embodiment, an entirely software embodiment (including firmware, resident software, micro-code, etc.) or an embodiment combining software and hardware aspects that may all generally be referred to herein as a "module" or "system." For example, a module may be implemented as a hardware circuit comprising custom circuits, gate arrays, off-the-shelf semiconductors such as logic chips, transistors, or other discrete components. A module may also be implemented at programmable hardware devices such as field programmable gate arrays, programmable array logic, programmable logic devices or the like.

Modules may also be implemented at software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Furthermore, aspects of the present inventive concepts may take the form of a computer program product embodied in one or more computer readable medium(s) having computer readable program code embodied thereon. A storage device can include a computer readable storage medium, which may be, for example, but not limited to, an electronic, magnetic, optical, electromagnetic, infrared, or semiconductor system, apparatus, or device, or any suitable combination of the foregoing. Any combination of one or more computer readable medium(s) may be utilized. The computer readable medium may be a computer readable signal medium or a computer readable storage medium. Examples of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While the inventive concepts has been shown and described with reference to specific embodiments, it should be understood by those skilled in the art that various changes in form and detail may be made therein without departing from the spirit and scope of the inventive concepts.

What is claimed is:

1. A computer-implemented method for displaying objects at a treatment display screen coupled to an apparatus for performing a treatment, comprising:

presenting a first arrangement of the objects at the treatment display screen, wherein the objects of the first arrangement of the objects are in a fixed state on the treatment display screen;

activating a rearrangement mode of operation of the treatment display screen, wherein the objects of the first arrangement of the objects are changed from the fixed state to a fluid state that allows for rearrangement of the objects of the first arrangement of the objects to a second arrangement of the objects that is different than the first arrangement of the objects, wherein the first arrangement of objects includes a first object at a first location of the display screen and a second object at a second location of the display screen;

preventing the treatment from being performed during operation in the rearrangement mode; and presenting the second arrangement of the objects at the treatment display screen during operation in the rearrangement mode, comprising:

moving the first object to the second location of the display screen;

determining that the rearrangement mode of operation is activated by displaying, at the treatment display screen, a connector or arrow that extends from the first object in a direction of the second location of the treatment display screen during the movement of the first object to the second location of the treatment display screen, the arrow or connector displayed to at least one of identify potential destination locations on the treatment display screen for moving the first object or illustrate how surrounding objects are impacted when the first object is moved to the second location; and repositioning the second object at a different location of the display screen than the second location, wherein the second arrangement of objects includes the first object at the second location of the treatment display screen and the second object is at the different location of the treatment display screen.

2. The computer-implemented method for claim 1, wherein the treatment includes a dialysis-related procedure.

3. The computer-implemented method for claim 1, wherein activating the rearrangement mode of operation comprises generating a unique key sequence.

4. The computer-implemented method for claim 1, wherein preventing the treatment from being performed comprises preventing an initiation of a treatment clock button displayed at the treatment display screen.

5. The computer-implemented method for claim 1, wherein the apparatus includes a dialysis system, and wherein the method further comprises:
   detecting a treatment-related event; and
   preventing the first arrangement of the objects from transitioning from the fixed state to the fluid state in response to detecting the treatment-related event.

6. The computer-implemented method for claim 5, wherein detecting the treatment-related event includes detecting blood in the dialysis system.

7. The computer-implemented method for claim 5, wherein detecting the treatment-related event includes detecting activation of a treatment clock button displayed at the treatment display screen.

8. The computer-implemented method for claim 1, further comprising, during operation in the rearrangement mode:
   determining a period of inactivity during which the objects remain at their current locations at the treatment display screen; and
   placing the objects in the fixed state in response to the period of inactivity.

9. The computer-implemented method for claim 1, further comprising:
   storing data related to the second arrangement of the objects;
   displaying a set of configuration options, a configuration option including the stored data related to the second arrangement of the objects; and
   selecting a configuration option from the configuration options.

10. The computer-implemented method for claim 9, wherein the configuration options are displayed in response to at least one of a power-related condition of a machine performing the treatment, an initialization of the treatment, and an activation of a treatment clock button displayed at the treatment display screen.

11. The computer-implemented method for claim 9, wherein the set of configuration options includes a default configuration.

12. The computer-implemented method for claim 9, further comprising identifying the configuration option including the stored data related to the second arrangement of the objects as being a recently used configuration.

13. The computer-implemented method for claim 1, wherein presenting the second arrangement of the objects at the treatment display screen comprises:
   determining that a first object in the fluid state is positioned on a second object;
   generating an object repository identified by a subscreen button; and
   placing the first object and the second object in the object repository.

14. The computer-implemented method for claim 1, wherein repositioning the second object at the different location comprises repositioning the second object to a location neighboring the second location.

15. The computer-implemented method for claim 14, wherein the first object and the second object are interchanged.

16. The computer-implemented method for claim 14, further comprising:
   assigning the objects to a display matrix at the treatment display screen, the display matrix comprising a plurality of columns and a plurality of rows; and
   determining a column and a row of the display matrix at which the first location and the second location are positioned, wherein moving the first object includes forming a vacancy at the first location, and wherein the vacancy at the first location is removed by moving an object adjacent the first location to the first location.

17. The computer-implemented method for claim 16, wherein the first object is moved to the column of the second location that is positioned to the left of the column of the first location, and wherein the second object is moved in a right direction of the treatment display screen.

18. The computer-implemented method for claim 16, wherein the first object is moved to the column of the second location that is positioned to the right of the column of the first location, and wherein the second object is moved in a left direction of the treatment display screen.

19. The computer-implemented method for claim 16, wherein the first object is moved to the row of the second location that is positioned above the column of the first location, and wherein the second object is moved in a down direction of the treatment display screen.

20. The computer-implemented method for claim 16, wherein the first object is moved to the row of the second location that is positioned below the column of the first location, and wherein the second object is moved in an up direction of the treatment display screen.

21. The computer-implemented method for claim 1, further comprising after presenting the second arrangement of the objects at the treatment display screen:
   transitioning the second arrangement of the objects from the fluid state to a fixed state; and
   permitting performance of the treatment.

22. A computer-implemented method for rearranging objects displayed at a treatment display screen, comprising:
   displaying the objects having a fixed state;
   suspending a medical treatment;
   placing the objects into a fluid state;
   rearranging the objects at the treatment display screen, comprising:
     moving a first object from a first location to a second location of the treatment display screen;
     determining that a rearrangement mode of operation is activated by displaying, at the treatment display screen, a connector or arrow that extends from the first object in a direction of the second location of the treatment display screen during the movement of the first object to the second location of the treatment display screen, the arrow or connector displayed to at least one of identify potential destination locations on the treatment display screen for moving the first object or illustrate how surrounding objects are impacted when the first object is moved to the second location;

repositioning a second object from the second location to a different location of the display screen than the second location; and transitioning the rearranged objects from the fluid state to the fixed state after rearranging the objects.

23. The computer-implemented method for claim 22, wherein the medical treatment includes a dialysis-related procedure.

24. The computer-implemented method for claim 22, wherein suspending the medical treatment comprises preventing an initiation of a treatment clock button displayed at the treatment display screen.

25. The computer-implemented method for claim 24, wherein placing the objects into the fluid state comprises generating a unique key sequence.

26. The computer-implemented method for claim 22, wherein the treatment display screen is in electronic communication with a dialysis system, and wherein the method further comprises:

detecting a treatment-related event; and preventing the objects from entering the fluid state in response to detecting the treatment-related event.

27. The computer-implemented method for claim 26, wherein detecting the treatment-related event includes detecting blood in the dialysis system.

28. The computer-implemented method for claim 26, wherein detecting the treatment-related event includes detecting activation of a treatment clock button displayed at the treatment display screen.

29. The computer-implemented method for claim 26, wherein the set of configuration options includes a default configuration.

30. The computer-implemented method for claim 26, further comprising identifying the configuration option including the stored data related to the rearranged objects as being a recently used configuration.

31. The computer-implemented method for claim 22, further comprising:

determining a period of inactivity during which the objects remain at their current locations at the treatment display screen; and placing the objects in the fixed state in response to the period of inactivity.

32. The computer-implemented method for claim 22, further comprising:

storing data related to the objects;

displaying a set of configuration options, a configuration option including the stored data related to the objects; and selecting a configuration option from the configuration options.

33. The computer-implemented method for claim 32, wherein the configuration options are displayed in response to at least one of a power-related condition of a machine performing the medical treatment, an initialization of the medical treatment, and an activation of a treatment clock button displayed at the treatment display screen.

34. The computer-implemented method for claim 22, wherein rearranging the objects at the treatment display screen comprises:

determining that a first object in the fluid state is positioned on a second object;

generating an object repository identified by a subscreen button; and placing the first object and the second object in the object repository.

35. The computer-implemented method for claim 22, wherein rearranging the objects at the treatment display screen comprises:

moving a first object from a first location at the treatment display screen to a second location at the treatment display screen; and repositioning a second object at the second location to another location.

36. The computer-implemented method for claim 35, wherein repositioning the second object at the second location to another location comprises repositioning the second object at the second location to a location neighboring the second location.

37. The computer-implemented method for claim 35, wherein the first object and the second object are interchanged.

38. A computer-implemented method for rearranging a plurality of objects displayed at a treatment display screen, comprising:

transitioning a plurality of objects from a fixed state to a fluid state;

moving a first object of the plurality of objects from a first location at the treatment display screen to a second location at the treatment display screen;

determining that a rearrangement mode of operation is activated by displaying, at the treatment display screen, a connector or arrow that extends from the first object in a direction of the second location of the display screen during the movement of the first object to the second location of the display screen, the arrow or connector displayed to at least one of identify potential destination locations on the treatment display screen for moving the first object or illustrate how surrounding objects are impacted when the first object is moved to the second location;

positioning the first object on or near a second object at the second location of the treatment display screen;

replacing, in a rearrangement mode, the first object and the second object at the treatment display screen with a subscreen button at the second location of the treatment display screen in response to a determination that the first object is positioned on or near the second object at the second location on the treatment display screen; and redisplaying at least one of the first object and the second object at the second location of the treatment display screen in response to selecting the subscreen button.

39. A computer-implemented method for rearranging a plurality of objects displayed at a treatment display screen, comprising:

rearranging a plurality of objects by transitioning the objects from a first fixed state to a fluid state;

determining that a rearrangement mode of operation is activated by displaying, at the treatment display screen, during rearrangement of the objects a connector or arrow that extends from the first object in a direction of the second location of the display screen during the movement of the first object to the second location of the display screen, the arrow or connector displayed to at least one of identify potential destination locations on the treatment display screen for moving the first object or illustrate how surrounding objects are impacted when the first object is moved to the second location;

positioning the first object on or near a second object at the second location of the treatment display screen;

determining a desired end location of the first object in the fluid state with respect to the second object;

generating an object repository if the first object is placed on top of a second object at the second location identified by a subscreen button, the method further comprising at least one of:

redisplaying the first and second objects interchanged with each other and in a second fixed state by replacing, in a rearrangement mode, the first object and the second object at the treatment display screen with a subscreen button at the second location of the treatment display screen in response to a determination that the first object is positioned on or near the second object at the second location on the treatment display screen; or repositioning the second object at a different location of the display screen than the second location, wherein the arrangement of the objects includes the first object at the second location of the treatment display screen and the second object is at the different location of the treatment display screen.

* * * * *